US006306580B1

(12) United States Patent
Pelletier et al.

(10) Patent No.: US 6,306,580 B1
(45) Date of Patent: Oct. 23, 2001

(54) PREPARATION OF HUMAN PAPILLOMAVIRUS E1 HAVING HELICASE ACTIVITY AND METHOD THEREFOR

(75) Inventors: Alex Pelletier, Fabreville; Chris M. Farnet, Outremont, both of (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 09/300,909

(22) Filed: Apr. 28, 1999

Related U.S. Application Data

(60) Provisional application No. 60/083,942, filed on May 1, 1998.
(51) Int. Cl.⁷ .............................. C12Q 1/70; C12Q 1/68; G01N 33/53
(52) U.S. Cl. ................... 435/5; 435/6; 435/7.71; 435/7.72; 435/7.45
(58) Field of Search .................... 435/5, 6, 7.71, 435/7.72, 7.45

(56) References Cited

U.S. PATENT DOCUMENTS 5,464,936  11/1995  Botchan et al. .

OTHER PUBLICATIONS

Hughes et al, Nucleic Acid Research, 1993, vol. 21, No. 25, pp. 5817–5823.*
Bream, G.L. et al., "Characterization of Human Papillomavirus Type 11 E1 and E2 Proteins Expressed in Insect Cells", Journal of Virology, 1993, pp. 2655–2663, vol. 67, No. 5.
Liu, J–S. et al., "The Functions of Human Papillomavirus Type 11 E1, E2 and E2C Proteins in Cell–free DNA Replication", Journal of Biological Chemistry, 1995, pp. 27283–27291, vol. 270, No. 45.
Mohr, I. J. et al., "Targeting the E1 Replication Protein to the Papillomavirus Origin of Replication by Complex Formation with the E2 Transactivator", Science, 1990, pp. 1694–1699, vol. 250.

Kuo, S–R et al., "Cell–free Replication of the Human Papillomavirus DNA with Homologous Viral E1 and E2 Proteins and Human Cell Extracts", Journal of Biological Chemistry, 1994, pp. 24058–24065, vol. 269, No. 39.
Jenkins, O. et al., "Characterization of the Helicase and ATPase Activity of human Papillomavirus Type 6b E1 Protein", Journal of General Virology, 1996, pp. 1805–1809, vol. 77.
Seo, Y–S. et al., "Bovine Papilloma Virus (BPV)–encloded E1 protein contains multiple activies required for BPV DNA replication", Proc. Natl. Acad. Sci. USA 1993, pp. 702–706, vol. 90.
MacPherson, P. et al., "The Bovine Papilloma Virus E1 Protein Has ATPase Activity Essential to Viral DNA Replication and Efficient Transfomration in Cells", Virology, 1994, pp. 403–408, vol. 204.
Seo, Y.–S. et al., "Bovine papilloma virus (BPV)–encoded E2 protein enhances binding of E1 protein to the BPV replication origin", Proc. Natl. Acad. Sci. USA, 1993, pp. 2865–2869, vol. 90.
Yang, Liu et al., "The E1 protein of bovine papilloma virus 1 is an ATP–dependent DNA helicase", Proc. Natl. Acad. Sci. USA, 1993, pp. 5086–5090, vol. 90.

* cited by examiner

*Primary Examiner*—Ali R. Salimi
(74) *Attorney, Agent, or Firm*—Robert P. Raymond; Alan R. Stempel; Mary-Ellen M. Devlin

(57) ABSTRACT

The present invention relates to a method for isolating cloned papillomavirus E1 protein from a eukaryotic expression system having demonstrable and reproducible viral helicase activity and preparation containing essentially pure E1 protein. The invention further relates to the use of this novel E1 protein preparation in a screening assay for identifying antiviral agents. More particularly a high throughput assay to screen for agents capable of inhibiting HPV DNA replication. The assay is based on measuring the effect of antiviral agents on the activity of the E1 protein and more specifically on its helicase activity.

23 Claims, 20 Drawing Sheets

1) E1, E2, origin interactions
2) E1 helicase activity
3) Interaction of E1/E2 with cellular replication proteins

```
                                                       % identity with
                                                           type 11
Low risk:
W1wl11    E1 protein - HPV  (type 11)   649aa
W1wl13    E1 protein - HPV  (type 13)   646aa
W1wl6     E1 protein - HPV  (type 6b)   649aa;           89%

High risk:
W1wl18    E1 protein - HPV  (type 18)   657aa;           51%
W1wl39    E1 protein - HPV  (type 39)   647aa
W1wl33    E1 protein - HPV  (type 33)   644aa
W1wl31    E1 protein - HPV  (type 31)   629aa;           55%
W1wl35    E1 protein - HPV  (type 35)   630aa
W1wlhs    E1 protein - HPV  (type 16)   506aa;           51%
W1wleb    E1 protein - BPV  (type  1)   605aa;           40%

1                                        33
(SEQ ID NO.13)  W1wl11   MADDSGTE.NE GSGCTGWFMV EAIVEHTTGT QIS
(SEQ ID NO.14)  W1wl13   MAEDTGTN.NE GTGCSGWFLV EAVVERTTGQ QIS
(SEQ ID NO.15)  W1wl 6   MADDSGTE.NE GSGCTGWFMV EAIVQHPTGT QIS
(SEQ ID NO.16)  W1wl18   MADPEGTD.GE GTGCNGWFYV QAIVDKKTGD VIS
(SEQ ID NO.17)  W1wl39   MANREGTD.GD GSGCNGWFLV QAIVDKQTGD TVS
(SEQ ID NO.18)  W1wl33   MADPEGTN.GA GMGCTGWFEV EAVIERRTGD NIS
(SEQ ID NO.19)  W1wl31   MADPAGTD.GE GTGCNGWFYV EAVIDRQTGD NIS
(SEQ ID NO.20)  W1wl35   MADPAGTDEGE GTGCNGWFFV EAVVSRRTGS SV.
(SEQ ID NO.21)  W1wlhs   .......... .......... .......... ...

34                                              77
W1wl11   EDEEEEV EDSGYDMVDF IDDRHI..TQNS .VEAQALFNRQ EADAHYA
W1wl13   DDEDETV EDSGLDMVDF IDDRPI..THNS .VEAQALLNEQ EADAHYA
W1wl 6   DDEDEEV EDSGYDMVDF IDDSNI..THNS .LEAQALFNRQ EADTHYA
W1wl18   DDEDENA TDTGSDMVDF IDTQGTFCEQAE LETAQALFHAQ EVHNDAQ
W1wl39   EDEDENA TDTGSDLADF IDDSTDICVQAE RETAQVLLHMQ EAQRDAQ
W1wl33   EDEDETA DDSGTDLLEF IDDSMENSIQAD TEAARALFNIQ EGEDDLN
W1wl31   EDENEDS SDTGEDMVDF IDNCNVYNNQAE AETAQALFHAQ EAEEHAE
W1wl35   EDENEDD CDRGEDMVDF INDTDILNIQAE TETAQALFHAQ EEQTHKE
W1wlhs   ....... .......... .......... .......... .......
```

FROM FIG. 2A

```
                78                                                              127
W1w111    TVQ DLKRKYLGSP YVSPISNVAN AVESEISPRL DAIKLTTQPK KVKRRLF
W1w113    AVQ DLKRKYLGSP YVSPLGHVEQ SVDCDISPRL DAIKLSRNSK KVKRRLF
W1w1 6    TVQ DLKRKYLGSP YVSPINTIAE AVESEISPRL DAIKLTRQPK KVKRRLF
W1w118    VLH VLKRKFAGGS TENSPLGERL EVDTELSPRL QEISLNSGQK KAKRRLF
W1w139    AVR ALKRKYTDSS GDTRPYGKKV GRNT..RGTL QEISLNVSST QATQTVY
W1w133    AVC ALKRKFAA.. ..CSQSAAED VVDRAANPCR TSINKNKECT YRKRKID
W1w131    AVQ VLKRKYVG.. ..SPLSDISS CVDYNISPRL KAICIENNSK TAKRRLF
W1w135    AVQ VLKRKYAS.. ..SPLSSVSL CVNNNISPRL KAICIENKNT AAKRRLF
W1w1hs    ............ ............ ............ ............ .......

128                                                             172
W1w111    ETR ELTDSGYGYS EVEA..ATQVEK HGDPE...NGGDG QERDTGRDIE GE
W1w113    QSR EITDSGYGYS ..EVEAETQVER NGEPE...NDCGG GGH..GRDKE GE
W1w1 6    QTR ELTDSGYGYS EVEAGTGTQVEK HGVPE...NGGDG QEKDTGRDIE GE
W1w118    ... TISDSGYGCS EVEATQIQVTTN GEHGGNVCSGGST EAIDNGGTEG NN
W1w139    ... SVPDSGYGNM EVETAEVEEVTV ATNT.....NGDA EGEHGGSVRE EC
W1w133    ... ELEDSGYGNT EVETQQMVQQVE SQNGDTNLNDLES SGVGDDSEVS CE
W1w131    ... ELPDSGYGNT EVETQQMVQVEE QQ..........T TLSCNGSDG. TH
W1w135    ... ELPDSGYGNS EVEIHEIQQVEG HD.........TV EQCSMGSGDS IT
W1w1hs    ... MLQVEGRHET ETPCSQYSGGSG GG..........C SQYSSGSGGE GV 173                                                             221
W1w111    GVEHREAE AVD.DSTREHA DTSGILELLK CKDIRSTLHG KFKDCFGLSF V
W1w113    GQVHTEVH TGS.Q.IEEHT GTTRVLELLK CKDVRATLYG KFKDCYGLSF T
W1w1 6    ..EHTEAE APT.NSVREHA GTAGILELLK CKDLRAALLG KFKECFGLSF I
W1w118    SSVDGTSD NSNIENVNPQC TIAQLKDLLK VNNKQGAMLA VFKDTYGLSF T
W1w139    SSVDSAID S...ENQDPKS PTAQIKLLLQ SNNKKAAMLT QFKETYGLSF T
W1w133    TNVDSCEN V.......... TLQEISNVLH SSNTKANILY KFKEAYGISF M
W1w131    SEREN..E T.......... PTRNILQVLK TSNGKAAMLG KFKELYGVSF M
W1w135    SSSDERHD E........T PTRDIIQILK CSNANAAMLA KFKELFGISF T
W1w1hs    SERHTICQ T.......... PLTNILNVLK TSNAKAAMLA KFKELYGVSF S 222                                                             270
W1w111    DLIRPFKSD RTTCADWVVA GFGIHHSIAD AFQKLIEPLS LYAHIQWLTN
W1w113    DLIRPFKSD KTTCGDWVVA AFGIHHSVSE AFEKLMQPLT TYMHIQWLTN
W1w1 6    DLIRPFKSD KTTCLDWVVA GFGIHHSISE AFQKLIEPLS LYAHIQWLTN
W1w118    DLVRNFKSD KTTCTDWVTA IFGVNPTIAE GFKTLIQPFI LYAHIQCLDC
W1w139    DLVRTFKSD KTTCTDWVAA IFGVHPTIAE GFKTLINKYA LYTHIQSLDT
```

FROM FIG. 2B

```
Wlwl33  ELVRPFKSD KTSCTDWCIT GYGISPSVAE SLKVLIKQHS LYTHLQCLTC
Wlwl31  ELIRPFQSN KSTCTDWCVA AFGVTGTVAE GFKTLLQPYC LYCHLQSLAC
Wlwl35  ELIRPFKSD KSTCTDWCVA AFGIAPSVAN .....FKHIT YVYIYNVYRV
Wlwlhs  ELVRPFKSN KSTCCDWCIA AFGLTPSIAD SIKTLLQQYC LYLHIQSLAC
```

```
               271                                              319
Wlwl11  AWGMVLLVLI RFKVNKSRCT VARTLGTLLN IPENHMLIEP PKIQSGVRA
Wlwl13  AWGMVLLVLI RFKVNKSRCT VARTLATFLN IPEDHMLIEP PKIQSSVAA
Wlwl 6  AWGMVLLVLL RFKVNKSRST VARTLATLLN IPENQMLIEP PKIQSGVAA
Wlwl18  KWGVLILALL RYKCGKSRLT VAKGLSTLLH VPETCMLIQP PKLRSSVAA
Wlwl39  KQGVLILMLI RYTCGKNRVT VGKGLSTLLH VPESCMLLEP PKLRSPVAA
Wlwl33  DRGIIILLLI RFRCSKNRLT VAKLMSNLLS IPETCMVIEP PKLRSQTCA
Wlwl31  SWGMVMLMLV RFKCAKNRIT IEKLLEKLLC ISTNCMLIQP PKLRSTAAA
Wlwl35  HGAMVILALL RFKVEKREQQ LKTIDAKLLC ISAASMLIQP PKLRSTPAA
Wlwlhs  SWGMVVLLLV RYKCGKNRET IEKLLSKLLC VSPMCMMIEP PKLRSTAAA
```

```
               320                                              368
Wlwl11  L YWFRTGISNA STVIGEAPEW ITRQTVIEHS LADSQFKLTE MVQWAYDN
Wlwl13  L YWFRTGISNA SIVTGETPEW IKRQTIVEHG LADNQFKLTE MVQWAYDN
Wlwl 6  L YWFRTGISNA STVIGEAPEW ITRQTVIEHG LADSQFKLTE MVQWAYDN
Wlwl18  L YWYRTGISNI SEVMGDTPEW IQRLTIIQHG IDDSNFDLSE MVQWAFDN
Wlwl39  L YWYRTGISNI SVVTGDTPEW IQRLTVIQHG IDDSVFDLSD MVQWAFDN
Wlwl33  L YWFRTAMSNI SDVQGTTPEW IDRLTVLQHS FNDNIFDLSE MVQWAYDN
Wlwl31  L YWYRTGMSNI SDVYGETPEW IERQTVLQHS FNDTTFDLSQ MVQWAYDN
Wlwl35  L YWFKTAMSNI SEVDGETPEW IQRQTVLQHS FNDAIFDLSE MVQWAYDN
Wlwlhs  L YWYKTGISNI SEVYGDTPEW IQRQTVLQHS FNDCTFELSQ MVQWAYDN
```

```
               369                                              418
Wlwl11  DI CEESEIAFEY AQRGDFDSNA RAFLNSNMQA KYVKDCAIMC RHYKHAEM
Wlwl13  DF CDESEIAFEY AQRGDFDSNA RAFLNSNCQA KYVKDCATMC KHYKNAEM
Wlwl 6  DI CEESEIAFEY AQRGDFDSNA RAFLNSNMQA KYVKDCATMC RHYKHAEM
Wlwl18  EL TDESDMAFEY ALLADSNSNA AAFLKSNCQA KYLKDCATMC KHYRRAQK
Wlwl39  EY TDESDIAFNY AMLADCNSNA AAFLKSNCQA KYVKDCATMC KHYKRAQK
Wlwl33  EL TDDSDIAYYY AQLADSNSNA AAFLKSNSQA KIVKDCGIMC RHYKKAEK
Wlwl31  DV MDDSEIAYKY AQLADSDSNA CAFLKSNSQA KIVKDCGTMC RHYKRAEK
Wlwl35  DF IDDSDIAYKY AQLAETNSNA CAFLKSNSQA KIVKDCATMC RHYKRAEK
Wlwlhs  DI VDDSEIAYKY AQLADTNSNA SAFLKSNSQA KIVKDCATMC RHYKRAEK
```

FROM FIG. 2C

```
             419                                                              466
W1wl11   KK  MSIKQWIKYR  GTKVDSVGNW  KPIVQFLRHQ  NIEFIPFLSK  LKLWLH
W1wl13   KK  MSMKQWITYR  SKKIEEAGNW  KPIVQFLRHQ  NIEFIPFLSK  LKLWLH
W1wl 6   RK  MSIKQWIKHR  GSKIEGTGNW  KPIVQFLRHQ  NIEFIPFLTK  FKLWLH
W1wl18   RQ  MNMSQWIRFR  CSKIDEGGDW  RPIVQFLRYQ  QIEFITFLGA  LKSFLK
W1wl39   RQ  MSMSQWIKFR  CSKCDEGGDW  RPIVQFLRYQ  GIEFISFLCA  LKEFLK
W1wl33   RK  MSIGQWIQSR  CEKTNDGGNW  RPIVQLLRYQ  NIEFTAFLGA  FKKFLK
W1wl31   RQ  MSMGQWIKSR  CDKVSDEGDW  RDIVKFLRYQ  QIEFVSFLSA  LKLFLK
W1wl35   RE  MTMSQWIKRR  CAQVDDDGDW  RDIVRFLRYQ  QVDFVAFLSA  LKNFLH
W1wlhs   KQ  MSMSQWIKYR  CDRVDDGGDW  KQIVMFLRYQ  GVEFMSFLTA  LKRFLQ 467                                                              516
W1wl11   GTPK  KNCIAIVGPP  DTGKSCFCMS  LIKFLGGTVI  SYVNSCSHFW  LQPLTD
W1wl13   GTPK  KNCIAIVGPP  DTGKSCFCMS  LIKFLGGTVI  SYVNSSSHFW  LQPLCN
W1wl 6   GTPK  KNCIAIVGPP  DTGKSYFCMS  LISFLGGTVI  SHVNSSSHFW  LQPLVD
W1wl18   GTPK  KNCLVFCGPA  NTGKSYFGMS  FIHFIQGAVI  SFVNSTSHFW  LEPLTD
W1wl39   GTPK  KNCIVIYGPA  NTGKSHFCMS  LMHFLQGTVI  SYVNSTSHFW  LEPLAD
W1wl33   GIPK  KSCMLICGPA  NTGKSYFGMS  LIQFLKGCVI  SCVNSKSHFW  LQPLSD
W1wl31   GVPK  KNCILIHGAP  NTGKSYFGMS  LISFLQGCII  SYANSKSHFW  LQPLAD
W1wl35   GVPK  KNCILIYGAP  NTGKSLFGMS  LMHFLQGAII  SYVNSKSHFW  LQPLYD
W1wlhs   GIPK  KNCILLYGAA  NTGKSLFGMS  LMKFLQGSVI  CFVNSKSHFW  LQPLAD 517                                                              566
W1wl11   AKVA  LLDDATQPCW  TYMDTYMRNL  LDGNPMSIDR  KHRALTLIKC  PPLLVT
W1wl13   AKVA  LLDDATQSCW  VYMDTYMRNL  LDGNPMSIDR  KHKSLALIKC  PPLLVT
W1wl 6   AKVA  LLDDATQPCW  IYMDTYMRNL  LDGNPMSIDR  KHKALTLIKC  PPLLVT
W1wl18   TKVA  MLDDATTTCW  TYFDTYMRNA  LDGNPISIDR  KHKPLIQLKC  PPILLT
W1wl39   AKLA  MLDDATGTCW  SYFDNYMRNA  LDGYAISLDR  KYKSLLQMKC  PPLLIT
W1wl33   AKIG  MIDDVTPISW  TYIDDYMRNA  LDGNEISIDV  KHRALVQLKC  PPLLLT
W1wl31   AKIG  MLDDATTPCW  HYIDNYLRNA  LDGNPVSIDV  KHKALMQLKC  PPLLIT
W1wl35   AKIA  MLDDATSPCG  IYRPIFKKCT  RWKSYISFRC  KALSIVHIM.  PTFTYY
W1wlhs   AKIG  MLDDATVPCW  NYIDDNLRNA  LDGNLVSMDV  KHRPLVQLKC  PPLLIT 567                                                              616
W1wl11   SNID  ISKEEKYKYL  HSRVTTFTFP  NPFPFDRNGN  AVYELSDANW  KCFFER
W1wl13   SNVD  ITKDDKYKYL  YSRVTTLTFP  NPFPFDRNGN  AVYELSDANW  KCFFTR
W1wl 6   SNID  ITKEDKYKYL  HTRVTTFTFP  NPFPFDRNGN  AVYELSNTNW  KCFFER
W1wl18   TNIH  PAKDNRWPYL  ESRITVFEFP  NAFPFDKNGN  PVYEINDKNW  KCFFER
W1wl39   SNTN  PVEDDRWPYL  RSRLTVFKFP  NAFPFDQNRN  PVYTINDKNW  KCFFEK
```

FROM FIG. 2D

```
W1w133    SNTN AGTDSRWPYL HSRLTVFEFK NPFPFDENGN PVYAINDENW KSFFSR
W1w131    SNIN AGKDDRWPYL HSRLVVFTFP NPFPFDKNGN PVYELSDKNW KSFFSR
W1w135    ININ AGKDDRWPYL HSRVVVFTFH NEFPFDKNGN PEYGLNDKNW KSFFSR
W1w1hs    SNIN AGTDSRWPYL HNRLVVFTFP NEFPFDENGN PVYELNDKNW KSFFSR 617                              649
W1w111   LSSS LDIEDSEDE.E D.GSNSQAFRC VPGSVVRTL.. (SEQ ID NO. 13)
W1w113   LSAS LDIQDSEDE.D D.GDNSQAFRC VPGTVVRTV.. (SEQ ID NO. 14)
W1w1 6   LSSS LDIQDSEDE.E D.GSNSQAFRC VPGTVVRTL.. (SEQ ID NO. 15)
W1w118   TWSR LDLHEEEEDAD TEGNPFGTFKL RAGQNHRPL.. (SEQ ID NO. 16)
W1w139   TWCR LDLQQDEDEGD NDENTFTTFKC VTGQNTRIL.. (SEQ ID NO. 17)
W1w133   TWCK LDLIEEEDK.E NHGGNISTFKC SAGENTRSLRS (SEQ ID NO. 18)
W1w131   TWCR LNLHEEEDK.E NDGDSFSTFKC VSGQNIRTL.. (SEQ ID NO. 19)
W1w135   TWCR LNLHEEEVK.E NDGDAFPAFKC VSGQNTRTLRD (SEQ ID NO. 20)
W1w1hs   TWSR LSLHEDEDK.E NDGDSLPTFKC VSGQNTNTL.. (SEQ ID NO. 21)
```

Fig. 2E

PURIFICATION PROCEDURE

FIGURE 5B
VALIDATION OF E1 HELICASE ACTIVITY - GEL ASSAY
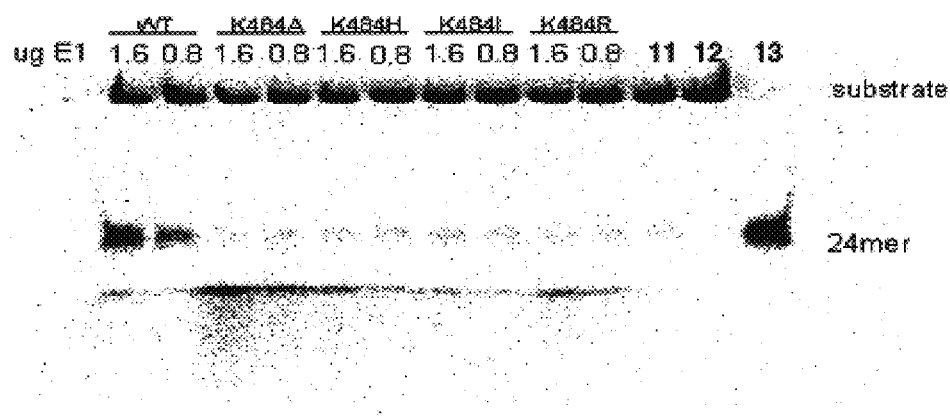
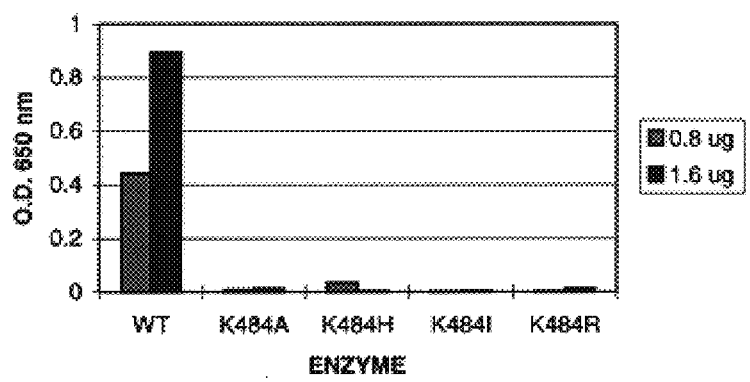
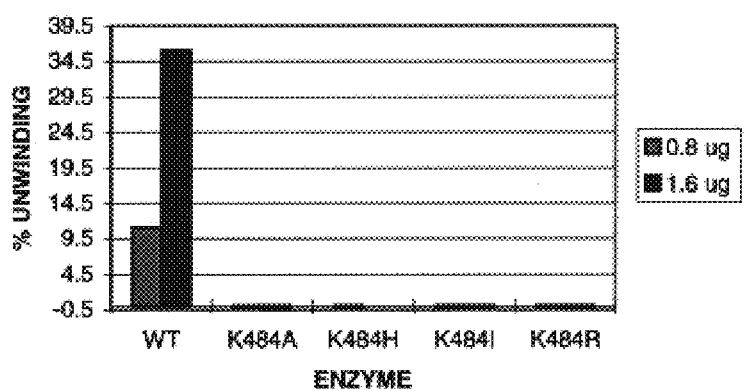

SCINTILLATION PROXIMITY ASSAY FOR E1 HELICASE 1 2 3 4 5 6 7

FIGURE 11

HPV-11 E1 (SEQ ID NO. 26)

```
Met Ala Asp Asp Ser Gly Thr Glu Asn Glu Gly Ser Gly Cys Thr Gly
Trp Phe Met Val Glu Ala Ile Val Glu His Thr Thr Gly Thr Gln Ile
Ser Glu Asp Glu Glu Glu Val Glu Asp Ser Gly Tyr Asp Met Val
Asp Phe Ile Asp Asp Arg His Ile Thr Gln Asn Ser Val Glu Ala Gln
Ala Leu Phe Asn Arg Gln Glu Ala Asp Ala His Tyr Ala Thr Val Gln
Asp Leu Lys Arg Lys Tyr Leu Gly Ser Pro Tyr Val Ser Pro Ile Ser
Asn Val Ala Asn Ala Val Glu Ser Glu Ile Ser Pro Arg Leu Asp Ala
Ile Lys Leu Thr Thr Gln Pro Lys Lys Val Lys Arg Arg Leu Phe Glu
Thr Arg Glu Leu Thr Asp Ser Gly Tyr Gly Tyr Ser Glu Val Glu Ala
Ala Thr Gln Val Glu Lys His Gly Asp Pro Glu Asn Gly Gly Asp Gly
Glu Glu Arg Asp Thr Gly Arg Asp Ile Glu Gly Glu Gly Val Glu His
Arg Glu Ala Glu Ala Val Asp Asp Ser Thr Arg Glu His Ala Asp Thr
Ser Gly Ile Leu Glu Leu Leu Lys Cys Lys Asp Ile Arg Ser Thr Leu
His Gly Lys Phe Lys Asp Cys Phe Gly Leu Ser Phe Val Asp Leu Ile
Arg Pro Phe Lys Ser Asp Arg Thr Thr Cys Ala Asp Trp Val Val Ala
Gly Phe Gly Ile His His Ser Ile Ala Asp Ala Phe Gln Lys Leu Ile
Glu Pro Leu Ser Leu Tyr Ala His Ile Gln Trp Leu Thr Asn Ala Trp
Gly Met Val Leu Leu Val Leu Ile Arg Phe Lys Val Asn Lys Ser Arg
Cys Thr Val Ala Arg Thr Leu Gly Thr Leu Leu Asn Ile Pro Glu Asn
His Met Leu Ile Glu Pro Pro Lys Ile Gln Ser Gly Val Ala Ala Leu
Tyr Trp Phe Arg Thr Gly Ile Ser Asn Ala Ser Thr Val Ile Gly Glu
Ala Pro Glu Trp Ile Thr Arg Gln Thr Val Ile Glu His Ser Leu Ala
Asp Ser Gln Phe Lys Leu Thr Glu Met Val Gln Trp Ala Tyr Asp Asn
Asp Ile Cys Glu Glu Ser Glu Ile Ala Phe Glu Tyr Ala Gln Arg Gly
Asp Phe Asp Ser Asn Ala Arg Ala Phe Leu Asn Ser Asn Met Gln Ala
Lys Tyr Val Lys Asp Cys Ala Ile Met Cys Arg His Tyr Lys His Ala
Glu Met Lys Lys Met Ser Ile Lys Gln Trp Ile Lys Tyr Arg Gly Thr
Lys Val Asp Ser Val Gly Asn Trp Lys Pro Ile Val Gln Phe Leu Arg
His Gln Asn Ile Glu Phe Ile Pro Phe Leu Ser Lys Leu Lys Leu Trp
Leu His Gly Thr Pro Lys Lys Asn Cys Ile Ala Ile Val Gly Pro Pro
Asp Thr Gly Lys Ser Cys Phe Cys Met Ser Leu Ile Lys Phe Leu Gly
Gly Thr Val Ile Ser Tyr Val Asn Ser Cys Ser His Phe Trp Leu Gln
Pro Leu Thr Asp Ala Lys Val Ala Leu Leu Asp Asp Ala Thr Gln Pro
Cys Trp Thr Tyr Met Asp Thr Tyr Met Arg Asn Leu Leu Asp Gly Asn
Pro Met Ser Ile Asp Arg Lys His Arg Ala Leu Thr Leu Ile Lys Cys
Pro Pro Leu Leu Val Thr Ser Asn Ile Asp Ile Ser Lys Glu Glu Lys
Tyr Lys Tyr Leu His Ser Arg Val Thr Thr Phe Thr Phe Pro Asn Pro
Phe Pro Phe Asp Arg Asn Gly Asn Ala Val Tyr Glu Leu Ser Asp Ala
Asn Trp Lys Cys Phe Phe Glu Arg Leu Ser Ser Ser Leu Asp Ile Glu
Asp Ser Glu Asp Glu Glu Asp Gly Ser Asn Ser Gln Ala Phe Arg Cys
Val Pro Gly Ser Val Val Arg Thr Leu
                                   649
```

FIGURE 12

HPV-6a E1 (SEQ ID NO. 27)

```
Met Ala Asp Asp Ser Gly Thr Glu Asn Glu Gly Ser Gly Cys Thr Gly
Trp Phe Met Val Glu Ala Ile Val Gln His Pro Thr Gly Thr Gln Ile
Ser Asp Asp Glu Asp Glu Glu Val Glu Asp Ser Gly Tyr Asp Met Val
Asp Phe Ile Asp Asp Ser Asn Ile Thr His Asn Ser Leu Glu Ala Gln
Ala Leu Phe Asn Arg Gln Glu Ala Asp Thr His Tyr Ala Thr Val Gln
Asp Leu Lys Arg Lys Tyr Leu Gly Ser Pro Tyr Val Ser Pro Ile Asn
Thr Ile Ala Glu Ala Val Glu Ser Glu Ile Ser Pro Arg Leu Asp Ala
Ile Lys Leu Thr Arg Gln Pro Lys Lys Val Lys Arg Arg Leu Phe Gln
Thr Arg Glu Leu Thr Asp Ser Gly Tyr Gly Tyr Ser Glu Val Glu Ala
Gly Thr Gly Thr Gln Val Glu Lys His Gly Val Pro Glu Asn Gly Gly
Asp Gly Gln Glu Lys Asp Thr Gly Arg Asp Ile Glu Gly Glu Glu His
Thr Glu Ala Glu Ala Pro Thr Asn Ser Val Arg Glu His Ala Gly Thr
Ala Gly Ile Leu Glu Leu Leu Lys Cys Lys Asp Leu Arg Ala Ala Leu
Leu Gly Lys Phe Lys Glu Cys Phe Gly Leu Ser Phe Ile Asp Leu Ile
Arg Pro Phe Lys Ser Asp Lys Thr Thr Cys Leu Asp Trp Val Val Ala
Arg Phe Gly Ile His His Ser Ile Ser Glu Ala Phe Gln Lys Leu Ile
Glu Pro Leu Ser Leu Tyr Ala His Ile Gln Trp Leu Thr Asn Ala Trp
Gly Met Val Leu Leu Val Leu Leu Arg Phe Lys Val Asn Lys Ser Arg
Ser Thr Val Ala Arg Thr Leu Ala Thr Leu Leu Asn Ile Pro Glu Asn
Gln Met Leu Ile Glu Pro Pro Lys Ile Gln Ser Gly Val Ala Ala Leu
Tyr Trp Phe Arg Thr Gly Ile Ser Asn Ala Ser Thr Val Ile Gly Glu
Ala Pro Glu Trp Ile Thr Arg Gln Thr Val Ile Glu His Gly Leu Ala
Asp Ser Gln Phe Lys Leu Thr Glu Met Val Gln Trp Ala Tyr Asp Asn
Asp Ile Cys Glu Glu Ser Glu Ile Ala Phe Glu Tyr Ala Gln Arg Gly
Asp Phe Asp Ser Asn Ala Arg Ala Phe Leu Asn Ser Asn Met Gln Ala
Lys Tyr Val Lys Asp Cys Ala Thr Met Cys Arg His Tyr Lys His Ala
Glu Met Arg Lys Met Ser Ile Lys Gln Trp Ile Lys His Arg Gly Ser
Lys Ile Glu Gly Thr Gly Asn Trp Lys Pro Ile Val Gln Phe Leu Arg
His Gln Asn Ile Glu Phe Ile Pro Phe Leu Thr Lys Phe Lys Leu Trp
Leu His Gly Thr Pro Lys Lys Asn Cys Ile Ala Ile Val Gly Pro Pro
Asp Thr Gly Lys Ser Tyr Phe Cys Met Ser Leu Ile Ser Phe Leu Gly
Gly Thr Val Ile Ser His Val Asn Ser Ser Ser His Phe Trp Leu Gln
Pro Leu Val Asp Ala Lys Val Ala Leu Leu Asp Asp Ala Thr Gln Pro
Cys Trp Ile Tyr Met Asp Thr Tyr Met Arg Asn Leu Leu Asp Gly Asn
Pro Met Ser Ile Asp Arg Lys His Lys Ala Leu Thr Leu Ile Lys Cys
Pro Pro Leu Leu Val Thr Ser Asn Ile Asp Ile Thr Lys Glu Asp Lys
Tyr Lys Tyr Leu His Thr Arg Val Thr Thr Phe Thr Phe Pro Asn Pro
Phe Pro Phe Asp Arg Asn Gly Asn Ala Val Tyr Glu Leu Ser Asn Thr
Asn Trp Lys Cys Phe Phe Glu Arg Leu Ser Ser Ser Leu Asp Ile Gln
Asp Ser Glu Asp Glu Glu Asp Gly Ser Asn Ser Gln Ala Phe Arg Cys
Val Pro Gly Thr Val Val Arg Thr Leu
                                    649
```

PREPARATION OF HUMAN PAPILLOMAVIRUS E1 HAVING HELICASE ACTIVITY AND METHOD THEREFOR

This application claims the benefit of U.S. Provisional Application No. 60/083,942, filed May 1, 1998.

FIELD OF THE INVENTION

The present invention relates to a method for isolating and purifying cloned papillomavirus (PV) E1 protein from a eukaryotic expression system, having demonstrable and reproducible viral helicase activity and devoid of contaminating activities. The invention further relates to the use of this novel protein extraction method to isolate substantially purified, preferably essentially pure, E1 protein having helicase activity to establish a screening assay for antiviral agents. More particularly the invention relates to E1 protein to establish a high throughput assay to screen for agents capable of inhibiting PV DNA replication. The assay is based on measuring the inhibition of the antiviral agents on the activity of the E1 protein and more specifically on its helicase activity.

BACKGROUND OF THE INVENTION

Papillomaviruses (PV) are non-enveloped DNA viruses that induce hyperproliferative lesions of the epithelia. The papillomaviruses are widespread in nature and have been recognized in higher vertebrates. Viruses have been characterized, amongst others, from humans, cattle, rabbits, horses, and dogs. The first papillomavirus was described in 1933 as cottontail rabbit papillomavirus (CRPV). Since then, the cottontail rabbit as well as bovine papillomavirus type 1 (BPV-1) have served as experimental prototypes for studies on papillomaviruses. Most animal papillomaviruses are associated with purely epithelial proliferative lesions, and most lesions in animals are cutaneous. In the human there are more than 75 types of papillomavirus (HPV) that have been identified and they have been catalogued by site of infection: cutaneous epithelium and mucosal epithelium (oral and genital mucosa). The cutaneous-related diseases include flat warts, plantar warts, etc. The mucosal-related diseases include laryngeal papillomas and anogenital diseases comprising cervical carcinomas (Fields, 1996, Virology, 3rd ed. Lippincott—Raven Pub., Philadelphia, N.Y.).

There are more than 25 HPV types that are implicated in anogenital diseases, these are grouped into "low risk" and "high risk" types. The low risk types include HPV type 6, type 11 and type 13 and induce mostly benign lesions such as condyloma acuminata (genital warts) and low grade squamous intraepithelial lesions (SIL). In the United States there are 5 million people with genital warts of which 90% is attributed to HPV-6 and HPV-11. About 90% of SIL is also caused by low risk types 6 and 11. The other 10% of SIL is caused by high risk HPVs.

The high risk types are associated with high grade SIL and cervical cancer and include most frequently HPV types 16, 18, 31, 33, 35, 45, 52, and 58. The progression from low-grade SIL to high-grade SIL is much more frequent for lesions that contain high risk HPV-16 and 18 as compared to those that contain low risk HPV types. In addition, only four HPV types are detected frequently in cervical cancer (types 16, 18, 31 and 45). About 500,000 new cases of invasive cancer of the cervix are diagnosed annually worldwide (Fields, 1996, supra).

Treatments for genital warts include physical removal such as cryotherapy, $CO_2$ laser, electrosurgery, or surgical excision Cytotoxic agents may also be used such as trichloroacetic acid (TCA), podophyllin or podofilox. Immunomodulatory agents are also available such as Interferon or Imiquimod. These treatments are not completely effective in eliminating all viral particles and there is either a high cost incurred or uncomfortable side effects related thereto. In fact, there are currently no effective antiviral treatments for HPV infection since with all current therapies recurrent warts are common (Beutner & Ferenczy, 1997, Amer. J. Med., 102(5A), 28–37).

The ineffectiveness of the current methods to treat HPV infections has demonstrated the need to identify new means to control or eliminate such infections. In recent years, efforts have been directed towards finding antiviral compounds, and especially compounds capable of interfering with viral replication at the onset of infection (Hughes, 1993, Nucleic Acids Res. 21:5817–5823). To that end, it has therefore become important to study the genetics of HPVs in order to identify potential chemotherapeutic targets to contain and possibly eliminate any diseases caused by HPV infections at the onset of infection. It is equally important to identify a measurable viral activity that demonstrates specificity and reliability to be used as an indicator in assessing the effectiveness of the potential chemotherapeutic agents against PVs.

The life cycle of PV is closely couple d to keratinocyte differentiation. Infection is believed to occur at a site of tissue disruption in the basal epithelium. As the infected cells undergo progressive differentiation the cellular machinery is maintained allowing viral gene expression to increase, with eventual late gene expression and virion assembly in terminally differentiated keratinocytes and the release of viral particles (Fields, supra).

The coding strands for each of the papillomavirus contains approximately ten designated translational open reading frames (ORFs) that have been classified as either early ORFs or late ORFs based on their location in the genome. E1 to E8 are expressed early in the viral replication cycle, and two late genes (L1 and L2) represent the major and minor capside proteins respectively. The E1 and E2 gene products function in viral DNA replication, whereas E5, E6 and E7 are expressed in connection with host cell proliferation. The L1 and L2 are involved in virion structure. The functions of E3, E4 and E8 gene products is uncertain at present.

Studies of HPV have shown that proteins E1 and E2 are both essential and sufficient for viral DNA replication in vitro (Kuo et al., 1994, J. Biol. Chem. 30: 24058–24065). This requirement is similar to that of bovine papillomavirus type 1 (BPV-1). Indeed, there is a high degree of similarity between E1 and E2 proteins and the ori-rsequences of all papillomaviruses (PV) regardless of the viral species and type (Kuo et al., 1994, supra). Of note, E1 is the most highly conserved protein in PV and its enzymatic activity is presumed to be similar for all PV types (Jenkins, 1996, J. Gen. Virol., 77:1805–1809).

Evidence emanating from studies of BPV-1 have shown that E1 possesses ATPase and helicase activities that are required in the initiation of viral DNA replication (Seo et al., 1993a, Proc. Natl. Acad. Sci. USA 90:702–706; Yang et al., 1993, Proc. Natl. Acad. Sci. 90:5086–5090; and MacPherson et al., 1994, 204:403–408).

The E2 protein is a transcriptional activator that binds to E1 protein and forms a complex that binds specifically to the ori sequence (see FIG. 1) (Mohr et al., 1990, Science 250:1694–1699). It is believed that E2 enhances binding of E1 to the BPV origin of replication (Seo et al., 1993b, Proc. Natl. Acad. Sci., 90:2865–2869). In HPV, Lui et al. suggested t hat E2 stabilizes E1 binding to the ori (1995, J. Biol. Chem., 270(45):27283–27291).

The helicase activity of the E1 proteins of papillomavirus therefore constitute a good molecular target to design chemical entities capable of inhibiting viral replication. Such objective requires that the E1 protein be extracted and purified to an extent where its helicase activity can be measured reliably and reproducibly. Such isolation of E1 helicase has however remained elusive or at best unreliable, especially on a scale sufficient to establish an assay to screen for such inhibitors.

Seo et al. (1993a, supra) disclose the extraction and purification of BPV-E1 from a baculovirus expression system with the step consisting of the use of PEG and 1 M NaCl in the nuclear extraction buffer. They obtained BPV-E1 preparation about 90% pure. However, we have not found it possible to obtain pure HPV-11 E1 by this procedure, and in any case the procedure is not suitable to the large scale required to purify E1 for high-throughput screening.

The two BPV-1 genes encoding E1 and E2 proteins have been cloned into a Baculovirus expression system and the proteins substantially purified (U.S. Pat. No. 5,464,936). U.S. Pat. No. '936 discloses a purification process for E1 consisting of a nuclear extraction in a hypertonic buffer (containing 300 mM NaCl) followed by 3 sequential chromatographic separations. The disclosure, however, does not demonstrate the purity and specific activity of the resulting E1 helicase. The absence of affinity chromatography purification step leads to the presence of contaminating nucleases that prevent accurate measurement of the E1 helicase activity. In addition, even if such a process would in fact yield E1 helicase of sufficient purity to assess the helicase activity, it is believed that it would be inapplicable to a high-yield, large-scale process for HTS purposes.

An extraction process wherein nuclei were suspended in lysis buffer containing 300 mM NaCl followed by further purification has been described (Bream et al., 1993, J. Virol., 2655). However, the authors were unable to detect helicase activity from these crude preparations of E1. Further attempts to isolate HPVs E1 protein cloned into different expression systems, having demonstrable and specific helicase activity, have failed (Jenkins et al., 1996, supra).

Kuo et al., 1994, supra discloses a purification procedure (using 420 mM salt during the nuclear extraction) but does not discuss the scale on which the procedure was carried out or the total yield of protein.

It has been hypothesized that the conformation of the E1 protein and its hydrophobicity cause the protein to be "sticky" and to form aggregates thus making it difficult to extract and purify. In addition, difficulties in establishing enzymatic activities that are specific and free of cellular contaminants have generally been encountered. For example, viral helicase and/or ATPase activity may not be distinguishable from cellular helicase and/or ATPase contaminants present in the host cell used to express the E1 gene. In addition, very low levels of nucleases will destroy the substrate rendering any assessment impossible.

One common denominator in the various purification processes outlined above lies in the presence of high concentrations of salt (hypertonic conditions) during the nuclear extraction step. Indeed, according to conventional wisdom, it is believed that nucleic acid-binding proteins may be solubilized in high concentrations of salt and thereby separated from nucleic acids. At present, the prior art has not revealed satisfactory processes for the purification of E1.

There thus remains a need to isolate a demonstrable and reproducible viral helicase activity that can be used as an indicator of the inhibitory effect of antiviral chemotherapeutic agents. More particularly, there remains a need to provide a method of preparing a PV E1 preparation displaying a high helicase activity.

There also remains a need to obtain a preparation of human papillomavirus E1 protein which displays a helicase activity sufficient for the purposes of a screening assay, particularly, a high throughput screening assay.

Since E1 structure/function is highly conserved amongst different papillomaviruses and amongst subtypes, it is assumed that the BPV and CRPV E1 proteins can be extracted and purified by the procedure of the invention. Therefore, there remains a need for a method for the isolation/purification of E1 protein from several species of papillomavirus, including, but not limited to bovine papillomavirus (BPV), cottontail rabbit papillomavirus (CRPV) and human papillomavirus (HPV). There also remains a need to isolate and purify the E1 protein from different subtypes of HPV, including but not limited to, HPV-6, 11, 16, 18, 31, 33, 35, 45, 52, and 58.

Before the present invention, E1 protein preparations, including human E1 preparations, did not demonstrate reproducible helicase activity. The deficiency in the prior art created a road block in being able to screen a large collection of antiviral agents capable of inhibiting papilloma viral DNA replication. This deficiency is overcome by the present invention which is capable of providing the means to design a HTS for the screening for such agents. The Applicant has now found a reliable and reproducible purification process for the preparation of E1 having helicase activity. The resulting E1 preparation is free from degradation products and amenable to large scale production of E1.

The present description refers to a number of documents, the content of which is herein incorporated by reference.

SUMMARY OF THE INVENTION

Therefore, in accordance with a first embodiment of the present invention, there is provided, a means for the isolation and purification of E1 protein having demonstrable, reliable and reproducible helicase activity.

Thus, the invention mostly concerns the isolation and purification of E1 protein from papillomavirus or a functional derivative thereof, having detectable helicase activity above background levels. The E1 preparation according to the present invention is significantly free of contaminating cellular helicase, ATPase and nuclease activities. The E1 preparation according to the present invention displays reproducible viral helicase activity.

In accordance with this first embodiment, there is provided a method for the isolation of the expressed E1 protein from the cloned E1 gene. There is therefore provided a method for extracting from a nuclear extract the papillomavirus E1 protein or a functional derivative thereof having viral helicase activity comprising the steps of:

a) producing an E1 recombinant protein in a eukaryotic expression system and isolating a nuclei preparation thereof;

b) extracting E1 protein from said nuclei preparation in a buffer comprising salt at a concentration lower than 300 mM.

This novel method for extracting E1 protein having helicase activity from a eukaryotic cell nuclei preparation, comprises the use of salt concentrations lower than those taught in the prior art.

There is further provided a method for isolating said E1 protein further comprising the step of:

c) purifying E1 protein from said nuclear extract by affinity chromatography.

The applicant was the first to design a method for the isolation of human papillomavirus E1 protein capable of demonstrating reproducible viral helicase activity, thus providing the essential element for the design of an assay for identifying potential antiviral agents capable of inhibiting E1 helicase activity and thereby preventing viral DNA replication. This method can also be applied for the isolation and purification of BPV and CRPV E1 helicases.

In accordance with a further aspect of the present invention, there is provided a preparation of recombinant papillomavirus E1 protein from a eukaryotic expression system, said E1 having viral helicase activity, wherein the E1 protein is extracted from a nuclei preparation in the presence of salt at a concentration less than 300 mM, and optionally purified by affinity chromatography.

In accordance with a further embodiment of the present invention, there is therefore provided the means to use the isolated E1 protein preparation in screening for the level of inhibition of candidate antiviral agents on E1 helicase activity.

There is therefore provided a method for assaying the specific viral helicase activity of papillomavirus E1 protein, said method comprising the steps of:

incubating a mixture of said E1 protein preparation as defined above, and a suitable substrate for said viral helicase enzymatic activity; and measuring the amount of specific helicase activity of said E1 protein.

There is further provided a method for identifying agents capable of modulating said helicase activity, said method comprising the steps of:

a) assaying the activity of said E1 helicase in the absence of said agent by the method as defined above;

b) assaying the activity of said helicase in the presence of said agent by the method as defined above, wherein said agent is added to said helicase and substrate mixture during said incubation; and c) comparing the result of step a) with the result of step b).

In accordance with a further embodiment, the isolated E1 protein has detectable and specific helicase activity, and, in the presence of E2 protein is capable of binding DNA to form a complex at the origin of replication, and contribute to viral DNA replication. Therefore, an alternative way to measure inhibition of E1 helicase activity is to measure the inhibition of viral DNA replication.

There is therefore provided a method for assaying papillomavirus DNA replication, said method comprising the steps of:

incubating a candidate agent with a mixture of E1 protein preparation as defined above, with E2 protein and a suitable DNA origin of replication; and measuring the amount of DNA unwinding.

There is also provided a method for identifying an agent capable of modulating papillomavirus DNA replication, said method comprising the steps of:

a) assaying said DNA replication activity in the absence of said agent by the method as defined above;

b) assaying said DNA replication activity in the presence of said agent by the method as defined above, wherein said agent is added to said mixture during said incubation; and c) comparing the result of step a) with the result of step b).

Other aspects of the present invention will become more apparent upon reading of the following non-restrictive description of preferred embodiments with reference to the accompanying drawing which is exemplary and should not be interpreted as limiting the scope of the present invention.

BRIEF DESCRIPTION OF THE DRAWINGS

Having thus generally described the invention, reference will now be made to the accompanying drawings, showing by way of illustration a preferred embodiment thereof, and in which:

FIGS. 2A TO 2E shows the alignment of the amino acid sequences of the E1 helicases of several papillomaviruses and shows their % identity compared to the sequence of the E1 helicase of HPV-11;

FIG. 5B shows three experiments with purified wild-type and mutants HPV-11 E1 proteins. The top panel shows the results of a helicase gel-based assay by detecting unwinding activity of the enzyme; the middle panel shows the results of an ATPase assay; and the bottom figure shows the results of a helicase assay, as detected by SPA. These experiments are described in Example 9;

FIG. 11 represents the amino acid sequence of HPV-11 E1 protein as isolated by the method of the invention. The amino acids in bold indicate the modifications observed compared to the published sequence of FIG. 2; and FIG. 12 represents the amino acid sequence of HPV-6a E1 protein as isolated by the method of the invention. The amino acid in bold indicates the modification observed compared to the published sequence of FIG. 2.

DETAILED DESCRIPTION OF PREFERRED EMBODIMENTS

Definitions

Figure 1:
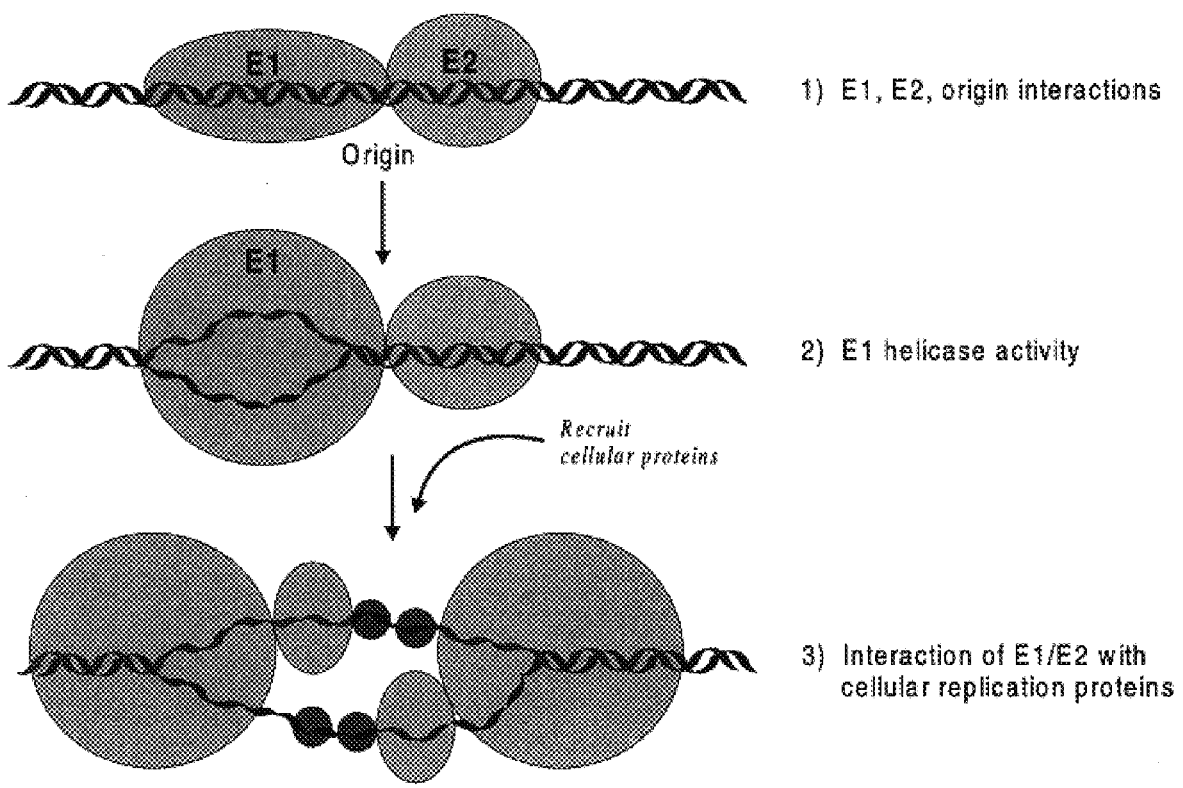
FIG. 1 shows a pictorial representation of the E1 and E2 interaction at the origin of replication of the papillomavirus. Briefly, the E1 protein is recruited at the origin of replication by the E2 protein and then forms a complex activating the helicase activity of the E1 to unwind DNA. The E1–E2 complex later recruits cellular replication proteins to eventually initiate DNA replication.

Unless defined otherwise, the scientific and technological terms and nomenclature used herein have the same meaning as commonly understood by a person of ordinary skill to which this invention pertains. Generally, the procedures for cell culture, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, N.Y.).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (Biochemistry, 1972, 11:1726–1732).

The present description refers to a number of routinely used recombinant DNA (rDNA) technology terms. Nevertheless, definitions of selected examples of such rDNA terms are provided for clarity and consistency.

The term "recombinant DNA" or "recombinant plasmid" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The term "oligonucleotide" or "DNA" molecule or sequence refers to a molecule comprised of the deoxyribonucleotides adenine (A), guanine (G), thymine (T) and/or cytosine (C). The term "oligonucleotide" or "DNA" can be found in linear DNA molecules or fragments, viruses, plasmids, vectors, chromosomes or synthetically derived DNA. As used herein, DNA sequences are described according to the normal convention of giving only the sequence in the 5' to 3' direction.

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise to a specific polypeptide or protein.

The term "fusion protein" as defined herein refers two polypeptidic segments that are not joined together in nature. Non-limiting examples of such "fusion proteins" according to the present invention include the E1 protein fused to the polypeptide of an "affinity label". In some embodiments it may be beneficial to introduce a cleavage site between the two polypeptide sequences which have been fused. Such protease cleavage sites between two heterologously fused protein are well known in the art.

The terms "vectors" or "DNA construct" are commonly known in the art and refer to any genetic element, including, but not limited to, plasmid DNA, phage DNA, viral DNA and the like which can incorporate the oligonucleotide sequences, or sequences of the present invention and serve as DNA vehicle into which DNA of the present invention can be cloned. Numerous types of vectors exist and are well known in the art.

The term "expression" defines the process by which a structural gene is transcribed into mRNA (transcription), the mRNA is then being translated (translation) into one polypeptide (or protein) more.

The terminology "expression vector" defines a vector or vehicle as described above but designed to enable the expression of an inserted sequence following transformation into a host. The cloned gene (inserted sequence) is usually placed under the control of control element sequences such as promoter sequences. Such expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

By "eukaryotic expression system" is meant the combination of an appropriate expression vector and a eukaryotic cell line which can be used to express a protein of interest. In some systems the gene for the protein may be inserted into the genome of a virus which can infect the cell type being used. Plasmid vectors containing the desired gene may also be used. In all cases, the vector will contain appropriate control elements (promoter) to express protein in the cell type of interest. Additional components, for example a vector or viral genome coding for T7 polymerase, may also be necessary in certain expression systems. Eukaryotic cell types typically used are yeast (e.g. *Saccharomyces cerevisiae, Pischia pastoris*) transfected with a plasmid vector; insect cells (e.g. SF9, SF21) infected with baculovirus (Autographa californica or Bombyx mori) (Luckow, Curr. Op. Biotech., 1993, 4:564–572; Griffiths and Page, 1994, Methods in Molec. Biol. 75:427–440; and Merrington et al., 1997, Molec. Biotech. 8(3):283–297); mammalian cells infected with adenovirus, vaccinia virus, Sindbis virus, or semliki forest virus; and mammalian cells transfected with DNA vectors for transient or constitutive expression. Particularly preferred here is the insect cell/baculovirus system.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting DNA may be maintained on an episomal element such as a plasmid. With respect to eukaryotic cells, a stably transfected cell is one in which the transfecting DNA has become integrated into a chromosome so that it is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989, supra; Ausubel et al., 1994, supra).

The term "affinity label" or "affinity tag" as used herein refers to a label which is specifically trapped by a complementary ligand. Examples of pairs of affinity marker/affinity ligand include but are not limited to: Maltose-Binding Protein (MBP)/maltose; Glutathione S Transferase (GST)/glutathione; histidine (His)/metal. The metal used as affinity ligand may be selected from the group consisting of: cobalt, zinc, copper, iron, and nickel (Wong et al. (1991), Separation and Purification Methods, 20(1), 49–106). Preferably, the metal selected is nickel. The affinity ligand can be set up in columns to facilitate separation by affinity chromatography.

The affinity label may be positioned on the N- or C-terminal end of the protein, but preferably on the N-terminus of the protein.

For certainty, the nucleotide sequences and polypeptides useful to practice the invention includes "functional derivatives". The term "functional derivatives" is intended to include "fragments", "segments", "variants", "analogs" or "chemical derivatives" of the subject matter of the present invention. The functional derivatives of the present invention can be synthesized chemically or produced through recombinant DNA technology. All these methods are well known in the art.

Thus, the term "variant" refers herein to a protein or nucleic acid molecule which is substantially similar in structure and biological activity to the protein or nucleic acid of the present invention.

As used herein, "chemical derivatives" is meant to cover additional chemical moieties not normally part of the subject matter of the invention. Such moieties could affect the physico-chemical characteristic of the derivative (i.e. solubility, absorption, half life and the like, decrease of toxicity). Such moieties are exemplified in Remington's Pharmaceutical Sciences (1980). Methods of coupling these chemical-physical moieties to a polypeptide are well known in the art.

As exemplified herein below, the nucleotide sequences and polypeptides used in the present invention can be modified, for example by in vitro mutagenesis, to dissect the catalytic and structure-function relationship thereof and permit a better design and identification of the resulting proteins. As used herein, the designation "functional derivative" denotes, in the context of a functional derivative of a sequence whether a nucleic acid or amino acid sequence, a molecule that retains a biological activity (either function or structural) that is substantially similar to that of the original sequence. This functional derivative or equivalent may be a natural derivatives or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid has chemico-physical properties which usually, but not necessarily, are similar to that of the substituted amino acid. The similar chemico-physical properties include, similarities in charge, bulkiness, hydrophobicity, hydrophilicity and the like. Some of the most commonly known conservative amino acid substitutions include, but are not limited to:

Leu or Val or Ile; Gly or Ala; Asp or Glu;
Asp or Asn or His; Glu or Gln; Lys or Arg;
Phe or Trp or Tyr; Val or Ala; Cys or Ser;
Thr or Ser; and Met or Leu.

As used herein, the term "purified" refers to a molecule having been separated from other cellular or viral components. Thus, for example, a "purified protein" has been purified to a level not found in nature.

The term "substantially purified" refers to a protein that is pure to about 60% or higher.

The term "substantially pure" refers to a protein that is pure to about 80% or higher.

The term "essentially pure" refers to a protein that is pure to about 90% or higher.

PREFERRED EMBODIMENTS

In a particularly preferred embodiment, the method of purification of E1 protein comprises an incubation of a nuclei extract from eukaryotic expression system at a salt concentration lower than 300 mM, preferably from 0–100 mM, more preferably from 0–50 mM and most preferably in the absence of salt.

Preferably, the salt refers to NaCl although other salts well known in the art (such as LiCl or KCl) may be used for nuclear extractions.

In accordance with a further embodiment of the invention, there is provided a method as described above wherein the E1 protein is the E1 helicase from bovine papillomavirus (BPV), cottontail rabbit papillomavirus (CRPV) or human papillomavirus (HPV). In a preferred embodiment, the E1 protein is from HPV low risk or high risk types. Preferably, when the E1 protein is a low risk type, it is selected from type 6, type 11 and type 13, and especially HPV type 11 and type 6. Alternatively, when the E1 protein is a high risk type, it is selected from the group consisting of types 16, 18, 31, 33, 35, 45, 52, or 58, preferably type 16.

A further aspect of the present invention provides the method as described above wherein the eukaryotic expression system is selected from the group consisting of: baculovirus in insect cells; Vaccinia, Sindbis, and Semliki forest viruses, or Adenovirus in mammalian cells (such as COS or Vero cells); and plasmid in yeast expression systems, preferably a baculovirus in insect cells expression system.

A further aspect of the present invention provides the method as described above wherein said E1 protein comprises an affinity label selected from the group consisting of: histidine tag, glutathione-S-transferase, and maltose-binding-protein and the complementary affinity ligand is selected from the group consisting of: antibody, nickel, maltose and glutathione columns.

Preferably, the antibody column comprises monoclonal or polyclonal antibodies, more preferably monoclonal antibodies.

Most preferably, the E1 protein is labeled with a histidine-tag and the His-labeled protein is separated on a nickel affinity ligand column.

Preferably, the affinity label is positioned at one terminus of the E1 protein, more preferably at the N-terminus thereof.

Still, a further aspect of the present invention provides a HPV E1 preparation prepared from low salt concentration, preferably extracted from a nuclei preparation in the presence of 0–100 mM NaCl, more preferably 0–50 mM NaCl, most preferably in the absence of NaCl, and further purified with affinity chromatography Preferably, the E1 preparation as described above is "substantially purified" at least about 60% purity and above, more preferably "substantially pure" at least about 80% purity and above, especially "essentially pure" at least about 90% purity.

Preferably, the E1 preparation as described above is the E1 helicase from bovine papillomavirus (BPV), cottontail rabbit papillomavirus (CRPV) or human papillomavirus (HPV), preferably from HPV low risk or high risk type. Preferably, when the E1 protein is a low risk type, it is selected from type 6, type 11 and type 13, and especially HPV type 11 and type 6. Alternatively, when the E1 protein is a high risk type, it is selected from the group consisting of types 16, 18, 31, 33, 35, 45, 52, or 58, preferably, type 16.

Methodology

The recombinant DNA constructs in accordance with the present invention can be constructed using conventional molecular biology, microbiology, and recombinant DNA techniques well known to those of skilled in the art (i.e. Sambrook et al, 1989, supra). With a suitable DNA construct transfected into a host cell, the present invention provides a method for the expression of a gene of interest. Alternatively, the DNA construct comprises a sequence coding for a affinity label, such as nucleotides coding for histidine (His). Transfection of the DNA construct into a host cell provides a convenient means for expressing a fusion protein comprised of the polypeptide of interest and the affinity label, thus allowing the isolation of the expressed fusion product by an affinity ligand column complementary to the affinity label.

Construction and Expression

We have used a particular version of the system from Gibco Lifesciences, in which the gene of interest is subcloned into a transfer vector which is then transformed into an E. coli strain containing a baculovirus genome. Specific sites on the vector then allow transposition which inserts the gene into the baculovirus genome (bacmid). This recombinant bacmid can then be isolated and transfected into SF9 or SF21 insect cells, which then produce the protein of interest, as well as infectious virus which can be used in the future to produce the protein of interest.

In other baculovirus systems, the gene of interest may be recombined into the baculovirus genome within the insect cell. This is done by transfecting insect cells with a vector containing the gene of interest and at the same time infecting them with baculovirus. In a certain percentage of the cases, the gene of interest is transferred to the viral genome by homologous recombination. Various methods well known in the art may be used to select for recombinant genomes carrying the gene of interest.

Extraction and Purification

The E1 protein of the invention can be purified using a specific protocol enabling it to be separated quickly and in a limited number of steps from the bulk of eukaryotic cellular and nuclear proteins and other viral contaminating components.

Contrary to conventional wisdom suggesting that nucleic acid binding proteins are more soluble in high salt concentrations, it has been established by the Applicant that the E1 protein is quickly and efficiently separated from the bulk of nuclear proteins and DNA by a low salt extraction protocol. Without wishing to be bound by theory, it is hypothesized that, when suspended in a hypotonic salt solution, the E1 protein leaches out selectively from the nucleus preparation. That is why the critical step of the invention comprises the low salt extraction of the E1 protein from nuclear extracts of HPV-infected baculovirus cell culture.

One of the peculiar aspect of the extraction protocol relies in the incubation time in which the nuclear extraction is carried out in the low salt solution (30–40 min as opposed to 5–10 min for the cell lysis). Indeed, in a preferred embodiment of the invention, the cell lysis buffer may also be hypotonic, however in this case it is important not to leave the lysed cells in the cell lysis buffer before the nuclei are centrifuged and separated to avoid E1 leaching in the lysis buffer prior to extraction.

Although our experiments allowed us to extract E1 at a salt concentration up to 500 mM, it was shown that some contaminants are observed at that concentration. It is therefore preferred to use salt concentrations that are below 300 mM, and preferably salt concentrations equal or below isotonic salt concentrations (150 mM) such as 100 mM, more preferably 50 mM, and most preferably, the extraction is carried out in the absence of salt.

Following the nuclear extraction, the E1 protein is preferably further purified via affinity chromatography.

For such purposes the protein can be expressed as a fusion protein comprising an affinity label which is specifically trapped by a complementary affinity ligand optionally bound to chromatographic column media. The affinity label is preferably localized on the N-terminus of the protein Examples of pairs of affinity label/affinity ligand column include but are not limited to: Maltose-Binding Protein (MBP)/maltose column; Glutathione S Transferase GST)/glutathione column; histidine (His)/Ni column.

In a preferred embodiment, the E1 is expressed as a His-E1 fusion protein and is purified through Ni column affinity chromatography according to methods well known in the art.

Alternatively, the protein can also be trapped by apolyclonal or monoclonal antibodies, in which case it does not need to be modified with a affinity label. For that purpose, an antiserum must be prepared.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", E1 sevier Science Publisher, Amsterdam, The Netherlands) and in Harlow et al., 1988 (in: Antibody—A Laboratory Manual, CSH Laboratories).

In accordance with an additional aspect of the present invention, there is provided the means for detecting antiviral agents using assays for screening their level of inhibition against HPV. The effectiveness of the candidate agents can be assessed by their ability to inhibit the viral helicase activity. This can be accomplished directly, by measuring the level of inhibition on the viral helicase activity or indirectly, by assessing the disruption on the interaction between the E1/E2/ori complex by measuring the inhibition on the viral DNA replication process.

Methods for detecting such antiviral agents include, without limitations, the use of colorimetric, fluorescent or radioactive reagents. Such detection methods can be applied in several types of assays such as culture plate assays or gel-based assays including for example Enzyme-Linked Immunosorbent Assay (ELISA), or Scintillation Proximity Assay (SPA) or any other assay well known in the art.

In one particular embodiment, there is provided an assay for screening and identifying candidate agents which modulate the helicase activity of E1, and more particularly the E1 helicase activity of HPV type 11 and type 6.

A preferred embodiment of such assay relies in a high throughput screening (HTS) assay for candidate agents capable of inhibiting E1 helicase activity and to identify such agents. Such high throughput screening assay is preferably selected from a fluorescence assay or a scintillation proximity assay, more preferably the latter.

Figure 6:
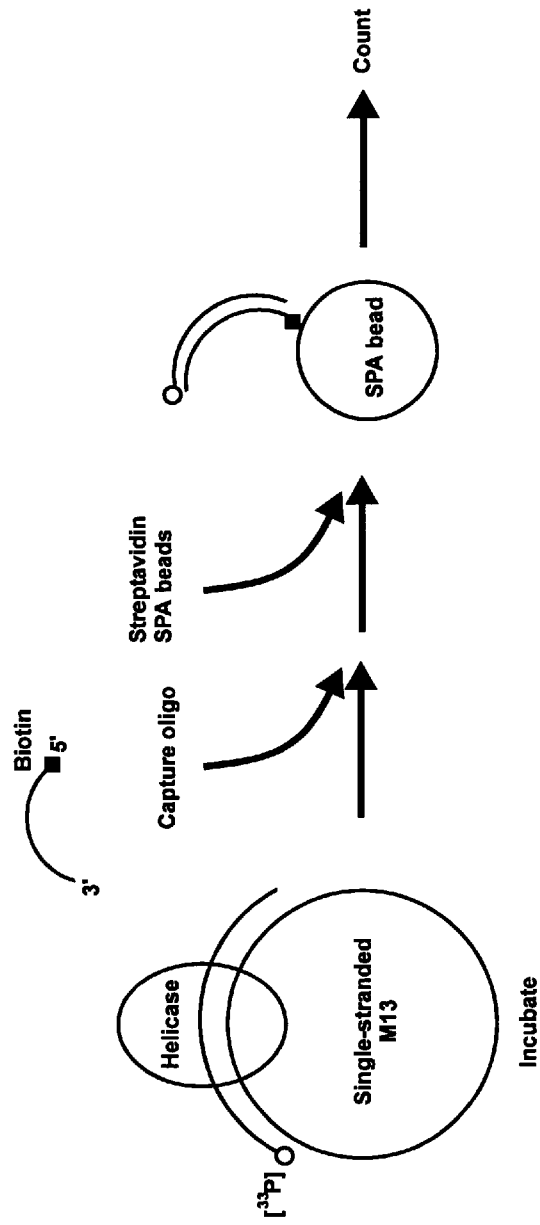
FIG. 6 shows a schematic representation of the high throughput screening assay for the E1 helicase as described in Example 11.

In this assay, the duplex DNA substrate consists of M13 single-stranded DNA (about 8000 bases) to which is annealed a 19 base oligodeoxynucleotide (see FIG. 6). This partial duplex is extended to 24 bases with the incorporation of [$^{33}$P]-labeled dATP by a reaction with the Klenow fragment of DNA polymerase I. Helicase activity results in the separation of this radiolabeled oligo from the M13 DNA. In the absence of a functional helicase, the double-stranded DNA substrate is stable for several hours at the assay temperature.

To detect activity, a second 24-base deoxyoligonucleotide, complementary to the substrate oligo, is added to the reaction mixture in a second step. This oligo anneals to any free radiolabeled oligo, but cannot interact with oligo still annealed to M13 DNA. A biotin is covalently attached to the 5'-terminus of the second oligo.

In the third step, streptavidin-coated SPA beads (Amersham Life Science, code TRKQ7030) are added to the mixture. The biotinylated oligo and any associated radiolabeled oligo then bind to these beads. SPA beads are impregnated with a scintillant, which allows detection of radiolabel in close proximity to the beads. Thus radiolabeled oligo annealed to the biotinylated oligo will be detected, whereas unreacted substrate still hybridized to M13 is not in close proximity to the beads and will not be detected.

In the presence of an inhibitor, less substrate is unwound, so a lower signal is detected. Positive controls used for the validation of this assay may be, among others cold substrate (such as the M13 single-stranded DNA) or DNA intercalators (such as ethidium bromide). The M13 DNA competes with the labeled M13 substrate and inhibits the signal detected. Ethidium bromide is a recognized DNA intercalator and stabilizes the M13-oligo substrate, thereby preventing helicase activity.

EXAMPLES

The present invention is illustrated in further detail by the following non-limiting examples.

Example 1: E1 Expression

Construction of recombinant plasmid

Recombinant baculovirus construct (Bac-to-Bac™ Baculovirus Expression Systems) (Gibco BRL): The E1 gene from HPV type 11 was pcr-amplified using recombinant plasmid pCR3-E1 as DNA template according to Lu et al. (1993, J. Virology 67:7131–7138). The forward primer was 5'-CGC GGA TCC AGG ATG CAT CAC CAT CAC CAT CAC GCG GAC GAT TCA CGT ACA GAA AAT GAG-3' (SEQ ID NO. 1) and the reverse was GG CTG AAT TCA TAA AGT TCT AAC AAC T (SEQ ID NO. 2). Purified pcr products were then restricted with EcoRI and BamHI and ligated with donor plasmid pFASTBAC1™ (Gibco, BRL) which had been linearized with the same enzymes.

HPV-11 E1 protein expression

His-E1-pFASTBAC was then transformed into *E. coli* strain DH10BaC™ for transposition following the manufacturer's instructions (Gibco-BRL). White colonies were selected and transposition confirmed by analytical pcr using primers flanking the bacmid (baculovirus circular DNA) insertion site.

Mini-preparation of recombinant bacmids was carried out and the purified bacmid DNA transfected into SF9 cells. Baculovirus-containing supernatants were collected 72 h post-transfection, and infected cells resuspended in 2× Leammli buffer for expression analysis by Western using anti-E1 K72 polyclonal antibody (see description of E2-dependent E1-DNA binding assay, Example 8). Recombinant baculovirus, confirmed to express His-E1 protein was reamplified and further used to infect SF21 insect cells for large scale production.

Example 2: HPV-11 His-E1 Extraction using Different Concentrations of Salt

E1 extraction. SF21 insect cells infected with E1-pFASTBAC recombinant baculovirus were harvested from 425 ml culture in SF-900 II SFM medium to give a cell pellet of 5 ml which has been frozen rapidly in dry ice. Frozen pellet was then thawed rapidly and cells resuspended in 5 ml of cell lysis buffer A (20 mM tris, pH 8.0, 1 mM DTT, 1 mM EDTA, 5 mM KCl, 1 mM MgCl$_2$—antipain, leupeptin and pepstatin each at 1 µg/ml–1 mM Pefabloc™). Following 15 min incubation on ice, cells were broken with a Dounce homogenizer (≈5 min, pestle B) and then centrifuged at 2500 g, 20 min, 4°. Pelleted nuclei were resuspended to 7 ml with resuspension buffer (20 mM Tris, pH 8.0, 1 mM DTT, 1 mM EDTA, antipain, leupeptin and pepstatin each at 2 µg/ml, 2 mM Pefabloc™) and distributed in 0,5 ml aliquots in 14 tubes. 0,5 ml of 13 different 2× extraction buffers (at varying concentrations of salt and detergents) were then mixed separately to 13 aliquots of nuclei, by pipetting up and down to give the final conditions listed below. Samples were incubated at 4° with rocking for 30 min and centrifuged in a microcentrifuge at maximal speed for 30 min. Supernatants were finally recovered and 4 µl of each run in 10% SDS-PAGE. 1 gel was stained with Coomassie Blue (FIG. 3A) and another one transferred for the membrane to be hybridized with anti-E1 K72 polyclonal antibody and detected with "western blot chemiluminescent reagent" (DuPont NEN, Boston, Mass.) and the emitted light was captured on autoradiography film (FIG. 3B).

Figure 3A:
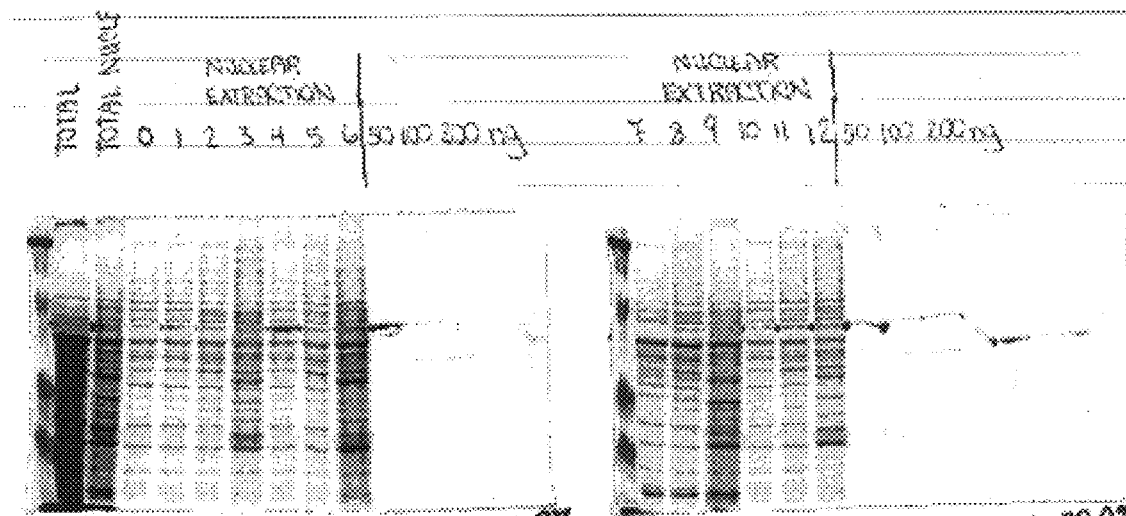
FIG. 3A shows a Coomassie blue-stained gel of different conditions for the nuclear extraction of the E1 protein according to the present invention (the legend of which is presented in Example 2)
Figure 3B:
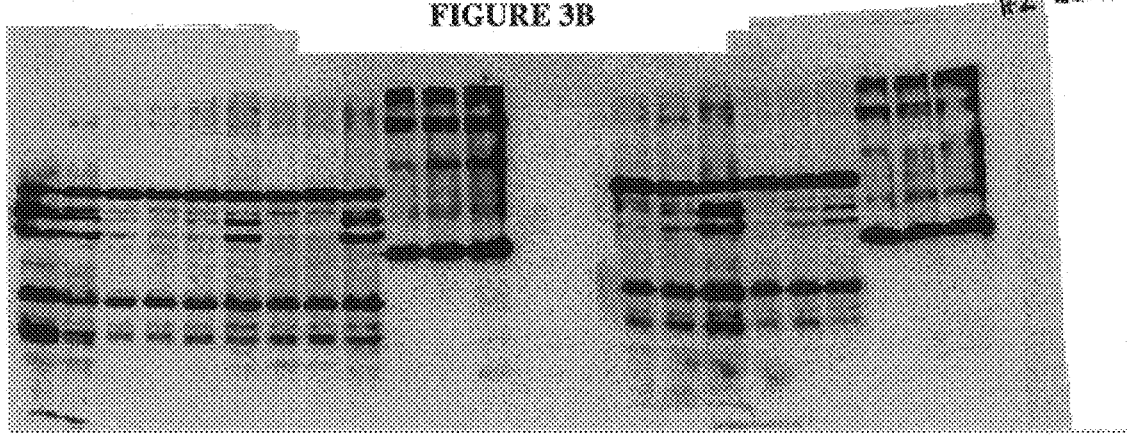
FIG. 3B shows a Western immunoblot of the gel of FIG. 3A, stained with an anti-E1 K72 polyclonal antibody and developed with a chemiluminescent reagent.

FIGS. 3A and 3B Legend:

Lane 0: 10 mM Tris, pH 8,0; 0,5 mM DTT; 0,5 MM EDTA

Lane 1: 20 mM tris, pH 8,0 ; 1 mM DTT; 0,5 MM EDTA

Lane 2: #1+100 mM NaCl

Lane 3: #1+450 mM NaCl

Lane 4: #1+0,01% Triton X-100

Lane 5: #1+0,01% Triton+100 mM NaCl

Lane 6: #1+0,01% Triton+450 mM NaCl

Lane 7: #1+0,1% Triton

Lane 8: #1+0,1% Triton+100 mM NaCl

Lane 9: #1+0,1% Triton+450 mM NaCl

Lane 10: #1+10% glycerol

Lane 11: #1+10% glycerol+100 mM NaCl

Lane 12: #1+10% glycerol+450 mM NaCl

Lanes indicated 50, 100, and 200 µg were samples of E1 fragment from *E. coli* that were used as positive control for the K72 antibody immunoblot.

FIGS. 3A and 3B show that the extraction of E1 from the nuclei preparation is not greatly improved by the use of detergent (lanes 4 to 12). As salt concentrations increase, more contaminants leach out of the nuclei. In absence of salt, almost all of the E1 protein is already extracted, and 100 mM does not show more E1 extracted. At 450 mM salt, the gel shows more contaminants and some degradation of the E1 protein.

Example 3: HPV-11 His-E1 Extraction

Cells infected with recombinant baculovirus were harvested and frozen rapidly in liquid nitrogen before being stored at −80°. For nuclear extraction, frozen cell pellets were thawed and resuspended in 1 volume (relative to the volume of cell pellet) of cell lysis buffer B containing protease-inhibitors (20 mM Tris pH 8, 5 mM β-mercaptoethanol, 5 mM KCl, 1 mM $MgCl_2$, 1 mM Pefabloc™, 1 μg/ml pepstatin, 1 μg/ml leupeptin, and 1 μg/ml antipain) and left on ice for 15 min. Cells were then broken on ice with a Dounce homogenizer (≈5 min, pestle B) followed by centrifugation at 2500 g, 4° for 20 min. Supernatant (cytosol) was discarded and nuclei resuspended to 1.4 volume with extraction buffer A (20 mM Tris pH 8, 5 mM β-mercaptoethanol, 2 mM Pefabloc™, 2 μg/ml pepstatin, 2 μg/ml leupeptin, and 2 μg/ml antipain). Finally, 1.4 volume of extraction buffer B (20 mM Tris pH 8, 5 mM β-mercaptoethanol, and 0.02% Triton X-100) was added and the nuclei incubated at 4° with rocking for 30 min before ultracentrifugation at 148,000 g, 40 for 45 min. Glycerol was added to the supernatant to 10% final concentration and the extract was frozen rapidly on dry ice and stored at −80°.

Example 4: HPV-11 His-E1 Purification

Nuclear extracts were thawed rapidly and the NaCl concentration adjusted to 500 mM before the preparation was loaded on 5 ml Hi-Trap™ chelating column previously charged with $NiSO_4$ according to the Manufacturer's instructions (Pharmacia, Biotech). The column was then pre-equilibrated in equilibration buffer (20 mM Tris pH 8, 5 mM β-mercaptoethanol, 500 mM NaCl, 10 mM imidazole, and 10% glycerol) and the flow-through collected for analysis. The column was washed first with 10 volumes of equilibration buffer and then with 10 volumes of washing buffer (equilibration buffer but with 50 mM imidazole) before His-E1 (or mutant proteins) was eluted (1 mL fractions 1 to 10) with elution buffer (equilibration buffer but with 180 mM imidazole). E1 proteins were then dialyzed in dialysis buffer (20 mM MES pH 7.0, 500 mM NaCl, 1 mM DTT, 0.05 mM EDTA, and 10% glycerol) before being frozen on dry ice and stored at −80°.

As an example of the yields obtained from this preparation, one 10 L preparation gave a 10 mL solution of purified E1 at 30 μg/mL (3 mg protein total).

Figure 4A:
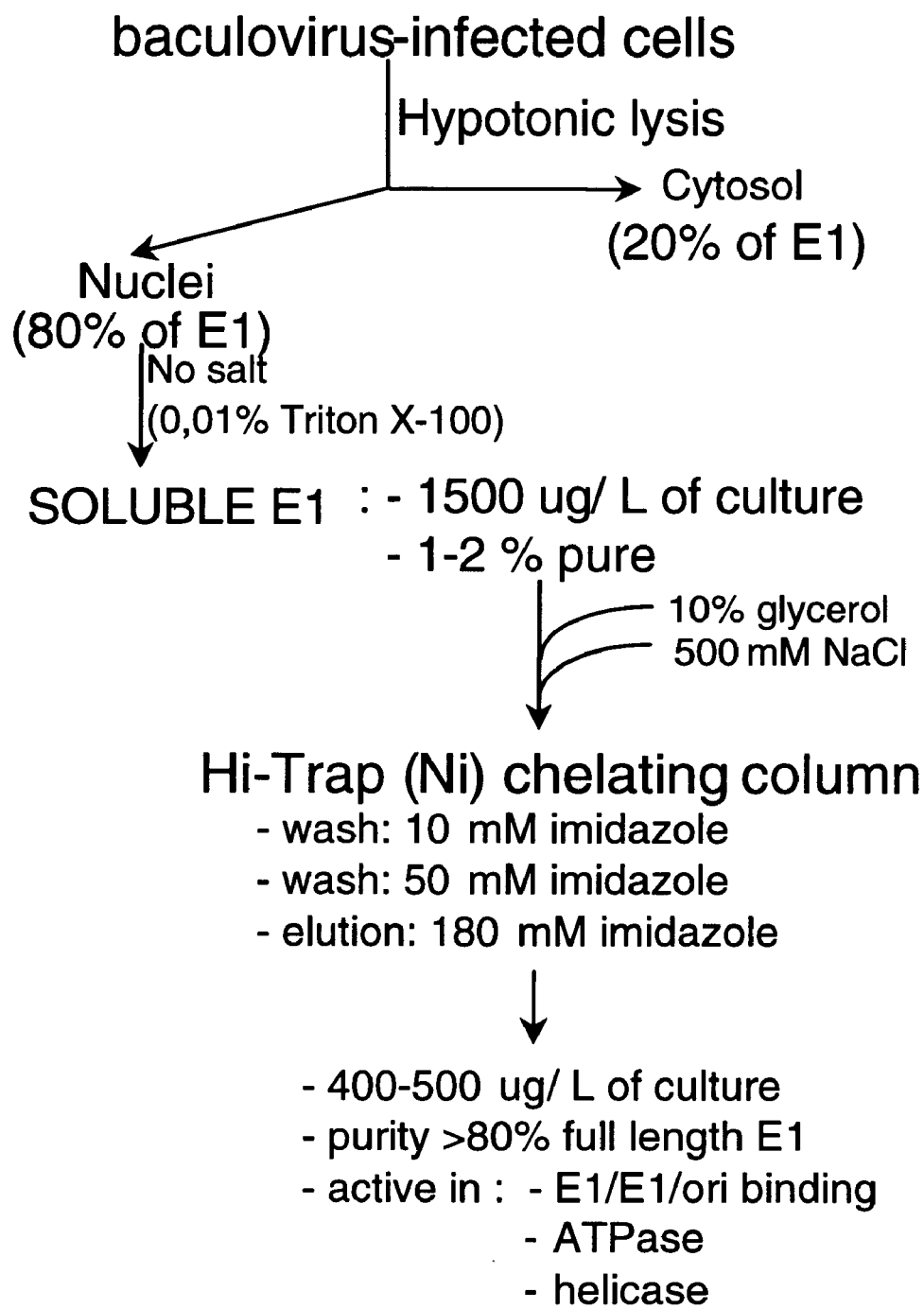
FIG. 4A shows a schematic representation of the purification process according to the invention.
Figure 4B:
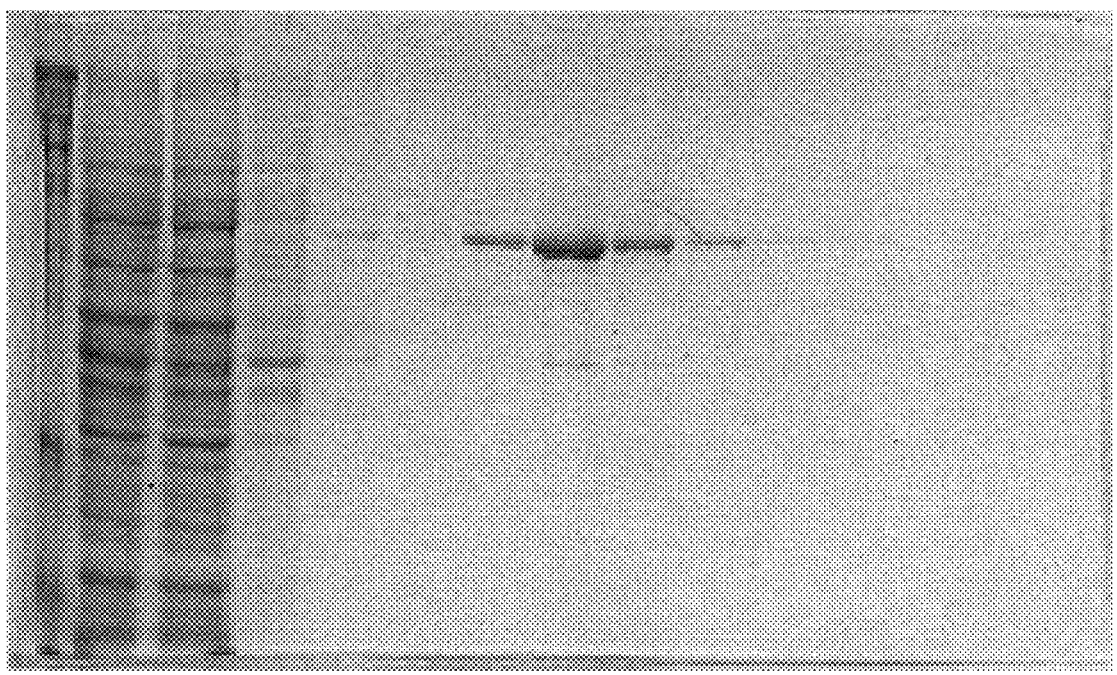
FIG. 4B shows a Coomassie blue-stained gel of the different fractions recovered from the affinity-chromatography purification (the legend of which is presented in Example 4)

Legend of FIG. 4B:
A: total load of the column;
B: flow-through;
C: equilibration with 10 mM imidazole;
D: washing with 50 mM imidazole;
Lanes 1 to 10 represent 1 mL fractions eluted with the elution buffer (180 mM imidazole).
FIG. 4B shows a Coomassie blue-stained gel where fractions 2, 3, and 4 contain most of the essentially pure E1 protein.

Example 5: Mutation Analysis of HPV-11 E1 Helicase

Mutant E1 proteins were made by disabling the helicase active site to validate that the helicase activity observed was due to the E1 protein and not to contaminants co-purified with E1.

Mutant plasmids encoding the K484A, K484H, K484I and, K484R mutations were constructed using the Quick-Change™ site-directed mutagenesis kit from Stratagene using the protocol supplied by the manufacturer.

The template for mutagenesis was the E1 DNA sequence carrying the K484E mutation. This mutant DNA template was used instead of wild type E1 because the K484E mutation creates a restriction site. This allowed us to identify quickly clones which carried the K484A, -H, -I, and -R mutations by simply screening for loss of the restriction site. The K484E mutation differed from the wild type E1 DNA sequence in the following way:

```
WT E1     5'-CCTGACACTGGGAAGTCGTGCTTTTGC-3'
          (SEQ ID NO. 3)

K4 84E    5'-CCTGACACTGGGGAGTCGTGCTTTTGC-3'
          (SEQ ID NO. 4)
```

(GAGTC is a site cut by the Ple 1 enzyme)
Pairs of complementary primers used for mutagenesis were:

```
K484A

MUT-TOP   5'-CCTGACACTGGGGCGTCGTGCTTTTGC-3'
          (SEQ ID NO 5)

MUT-BOT   5'-GCAAAAGCACGACGCCCCAGTGTCAGG-3'
          (SEQ ID NO. 22)

K484H

MUT-TOP   5'-CCTGACACTGGGCACTCGTGCTTTTGC-3'
          (SEQ ID NO. 6)

MUT-BOT   5'-GCAAAAGCACGAGTGCCCAGTGTCAGG-3'
          (SEQ ID NO. 23)

K484I

MUT-TOP   5'-CCTGACACTGGGATCTCGTGCTTTTGC-3'
          (SEQ ID NO. 7)

MUT-BOT   5'-GCAAAAGCACGAGATCCCAGTGTCAGG-3'
          (SEQ ID NO. 24)

K484R

MUT-TOP   5'-CCTGACACTGGGCGGTCGTGCTTTTGC-3'
          (SEQ ID NO 8)

MUT-BOT   5'-GCAAAAGCACGACCGCCCAGTGTCAGG-3'
          (SEQ ID NO 25)
```

The subcloning of these mutant alleles in baculovirus was amplified by pcr using the same primers as described above.

All His-E1-K484A, -H, -I, and -R constructs were cloned into the same pFASTBac™ vector, transformed into *E. coli* DH10Bac™ plasmids according to Example 1. The resulting bacmids were transfected in SF9 cells, and the recombinant viruses infected in SF21 cells also according to Example 1.

Example 6: HPV-11 E2 Protein Expression

HPV-11 E2 was obtained by expression in baculovirus-infected insect cells. A baculovirus encoding the gene for HPV-11 E2 was obtained from R. Rose (U. Rochester, N.Y.) and used to infect SF21 insect cells. Infected cells were resuspended in cell lysis buffer C (30 mM HEPES pH 7.6, 1 mM EDTA, 2 mM DTT, 1% NP-40, and protease inhibitors: 1 mM Pefabloc™, 1 mM PMSF, and 2.5 μg/mL each antipain, leupeptin, and pepstatin). Lysis occurred on stirring the cells, and nuclei were recovered by centrifugation. Nuclei were resuspended in nuclear extraction buffer C (30 mM HEPES pH 7.6, 10% glycerol, 250 mM NaCl, 5 mM EDTA, 2 mM DTT, 0.5% NP-40, and the same protease inhibitors as above). The suspension was stirred for 45 min, then sonicated. E2 was recovered in the supernatant following centrifugation.

Example 7: Purification of HPV-11 E2

E2 was purified from the nuclear extract using a DNA affinity chromatography by a procedure based on that of Seo et al. (PNAS 90(93) 2865). To prepare the affinity ligand column, duplex DNA containing three E2 binding sites was prepared by annealing two oligos (5'-biotin-AGT GAC CGA AAA CGG TCG GGA CCG AAA ACG GTG TAG ACC GAA AAC GGT GTA-3' (SEQ ID NO. 9) and 5'-CTA CAC CGT TTT CGG TCT ACA CCG TTT TCG GTC CCG ACC GTT TTC GGT CAC T-3' (SEQ ID NO. 10)). The duplex was bound to streptavidin agarose by virtue of the biotin incorporated into the first oligo. Chromatography was carried out using elution buffer D (nuclear extraction buffer C without protease inhibitors) and elution buffer E (elution buffer D plus 1M NaCl). A typical column consisted of 10 mL of the above resin. The nuclear extract was centrifuged at 50,000 g for 20 min. to remove any precipitated material, then applied to the column, washed with elution buffer D until the absorbance of the eluent at 280 nm reached baseline, then eluted with a linear gradient of elution buffers D and E, 60 mL of each. Fractions containing pure E2 (by SDS-PAGE) were pooled and concentrated to approximately 150 μg/mL using a Millipore centrifugal filter device (Ultrafree-15™), then stored at −80°.

Example 8: E2-dependent E1 DNA Binding Assay

This assay was modeled on a similar assay for SV40 T Antigen described by McKay (J. Mol. Biol., 1981,145:471). A 400 bp radiolabeled DNA probe, containing the HPV-11 origin of replication (Chiang et al., 1992, Proc. Natl. Acad. Sci. USA 89:5799) was produced by pcr, using plasmid pBluescript™ SK encoding the origin (nucleotides 7886-61 of the HPV-11 genome in unique BAMH1 site) as template and primers flanking the origin. Radiolabel was incorporated as [$^{33}$P]dCTP. Binding assay buffer consisted of: 20 mM Tris pH 7.6, 100 mM NaCl, 1 mM DTT, 1 mM EDTA.

Other reagents used were protein A-SPA beads (type II, Amersham) and K72 rabbit polyclonal antiserum, raised against a peptide corresponding to the C-terminal 14 amino acids of HPV-11 E1. Following the protocol from Amersham, one bottle of beads was mixed with 25 mL of binding assay buffer. For the assay, a saturating amount of K72 antiserum was added to the beads and the mixture was incubated for 1 h, washed with one volume of binding assay buffer, and then resuspended in the same volume of fresh binding assay buffer. Binding reactions contained 8 ng of E2, approximately 100–200 ng of purified E1, and 0.4 ng of radiolabeled probe in a total of 80 μL of binding assay buffer. After 1 h at room temperature, 25 μL of K72 antibody-SPA bead suspension was added to with the binding reaction and mixed. After an additional hour of incubation at room temperature, the reactions were centrifuged briefly to pellet the beads and the extent of complex formation was determined by scintillation counting on a Packard TopCount™. Typically, the signal for reactions containing E1 and E2 was 20–30 fold higher than the background observed when either E1, E2, or both was omitted.

Figure 5A:
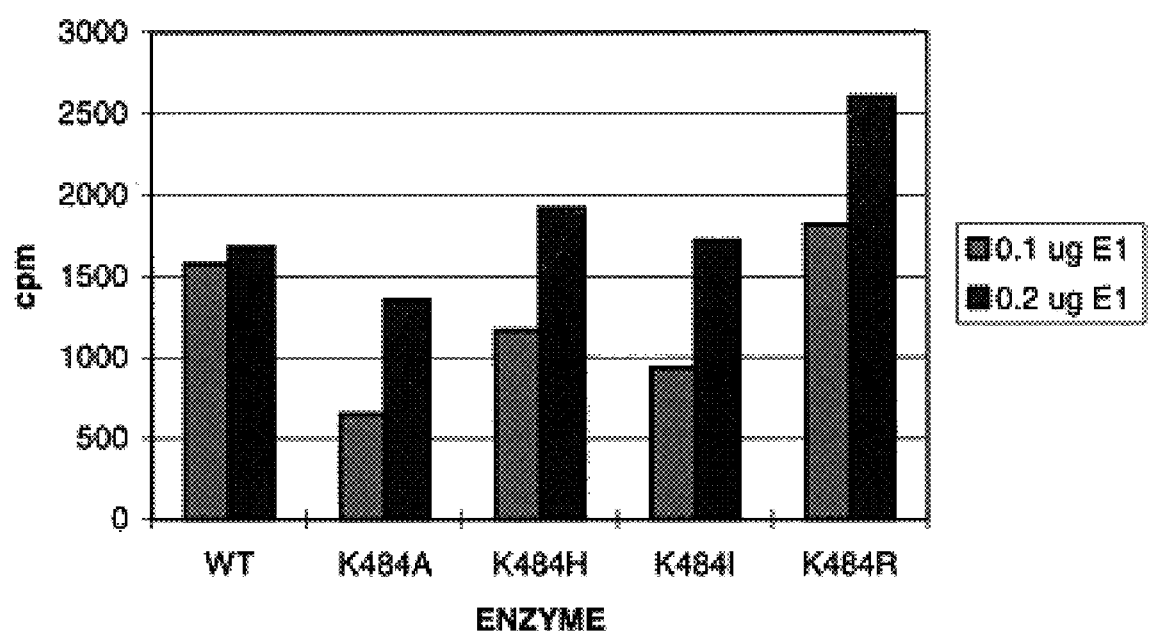
FIG. 5A shows the results of the E1/E2/ori binding assay described in Example 8.

FIG. 5A shows the DNA binding activity of the E1/E2 complex of the wild type (wt) E1 helicase and the four mutants produced in Example 5. There was no significant difference in the E1/E2/ori binding between any of the proteins indicating that the mutant proteins were folding in a normal fashion.

Example 9: Helicase/ATPase Assays

Helicase/ATPase assays

The substrate for the analytical helicase assay consisted of a 24-base oligonucleotide (GTA AAA CGA CCA GTG CCA AGC) (SEQ ID NO. 11) end-labeled using [$^{33}$P]ATP and polynucleotide kinase, annealed to M13mp18. Combined helicase/ATPase reactions contained 800 or 1600 ng of E1, 2 mM MgCl$_2$, 1 mM ATP, and 1 μM helicase substrate (concentration in nucleotides) in a total volume of 80 μL of helicase assay buffer (20 mM MES, pH 7.0, 1 mM DTT, 0.05 mM EDTA, 10% glycerol). Reactions were incubated for 2 h at 37° and then placed on ice.

Helicase gel-based detection:

25 μL of each reaction was mixed with 5× helicase stop/loading solution (12.5% Ficoll 4000, 0.5% SDS, 50 mM EDTA, and 0.125% each bromophenol blue and xylene cyanol); 20 μL of the mixture was electrophoresed for 1 h at 125 V through a 20% polyacrylamide/1× TBE gel. Blank reactions containing no enzyme were run in parallel. The gel was dried and scanned on a Molecular Dynamics PhosphorImager™. The substrate and reaction product separated by size, with the substrate remaining at the top of the gel and the unwound radiolabeled oligonucleotide migrating approximately half-way down.

In some cases degradation products due to nuclease activity are apparent further down the gel.

FIG. 5B top panel shows the gel migration of the helicase substrate and product after incubation with the wild-type (wt) and the mutants E1 proteins. Lane 13 is a boiled sample, lane 12 is a blank, whereas lane 11 is a blank which has been incubated for 2 h at 37°.

As apparent from FIG. 5B, none of the mutants show any significant helicase activity compared to the wild-type E1 protein.

The intensity of the unwound oligonucleotide band may be quantitated using the PhosphorImager™, and the amount of activity may be expressed relative to 100% unwinding as described below for the SPA.

ATPase assay

An additional 15 μL of each reaction was used to detect ATPase activity by the procedure of Lanzetta et al. (Anal. Biochem., 1979, 100, 95).

FIG. 5B middle panel shows that the ATPase activity follows the helicase activity as demonstrated by the gel assay.

Helicase Scintillation Proximity Detection (SPA)

An additional 30 μL was transferred to another 96-well plate containing 30 μL of SPA stop hybridization buffer, which is identical to the "stop" buffer in Example 11, except that the biotinylated capture oligonucleotide is complementary to the substrate sequence above.

Helicase activity was quantitated as follows:

A separate reaction mixture, containing no enzyme was heated to 95° for 10 min., and the resulting free substrate oligonucleotide (completely denatured) was detected as described for reaction mixtures. The level of signal generated in this experiment represents 100% unwinding. Similar samples, which were not heated, serve a blanks, representing background signal. Quantitation of unwinding is calculated relative to the boiled sample with background subtracted.

FIG. 5B bottom panel shows that the percent of unwinding is negligible with the mutant proteins as compared to the wild-type (wt) control. These results are in accordance with the ones obtained from the gel-based assay.

Example 10: Enzymatic Activity

His-E1 helicase specific activity

Enzymatic Activities of HPV-11 E1-Comparison to Literature

TABLE 1

| Helicase Activity | V (% unwinding/ $\mu$M protein/min) | Reference |
|---|---|---|
| HPV-11 E1 | 2.5 | this work |
| HPV-6a E1 | 2.3 | this work |
| SV-40 TAg | 5.0 | this work |
| BPV E1 | 2.9 | Yang, PNAS (1993) |

Table 1 compares the enzymatic activity of the helicase from HPV-11 and -6 as purified according to the present invention, to another helicase reported in the literature. This represents the first instance where the human papillomavirus helicase E1 is purified to an extent where its unwinding activity can be quantified.

In all cases the enzyme concentration was greater than the substrate concentration and the substrate was partial duplex DNA. All experiments were done at 37° except for the BPV-E1 which was assayed at 32°. The SV-40 TAg was also assessed in the literature and V of 50 and 80 % unwinding/ $\mu$m protein/min were obtained from these groups respectively (Goetz, JBC (1988); Stahl, EMBO (1986)). The extent of the difference with our results stem from the fact that our assay conditions were optimized for E1 activity and may not be optimal for TAg activity (lower pH, etc.).

Example 11: High-throughput Screening Assay

SPA references:

N. Bosworth, P. Towers, "Scintillation proximity assay" *Nature* 341, 167–168 (1989).

N. D. Cook, "Scintillation proximity assay- a versatile high throughput screening technology" *Drug Discovery Today*, 1, 287–294 (1996).

"Determination of DNA helicase activity using a [$^3$H] scintillation proximity assay (SPA) system" Proximity News, July 1996.

This assay is similar to that in Example 9. The radiolabeled DNA substrate for this assay consists of a 19-base oligonucleotide (TTC CCA GTC ACG ACG TTG T) (SEQ ID NO 12) annealed to single-stranded M13mp18 plasmid. The Klenow fragment is used to extend the partial duplex to 24 bases, using four [$^{33}$P]dATP and one unlabeled dCTP.

Helicase reactions are run by mixing 10 $\mu$L each of the following components:

1) a substrate cocktail comprising radiolabeled DNA substrate, ATP, and magnesium acetate;
2) inhibitors dissolved in buffer plus 18% DMSO;
3) HPV-11 E1 purified as in Example 4.

Assay buffer, used for all dilutions, consisted of 20 mM MES, pH 7.0, 10% glycerol, 1.0 mM DTT, and 0.05 mM EDTA. Final concentrations in the assay are 0.8 $\mu$M (concentration in nucleotides), 1.0 mM ATP, 1.0 mM magnesium acetate, 6% DMSO. Sufficient E1 is used to give approximately 20% unwinding (as determined in Example 9). Reaction mixtures are incubated at 37° for 2 h in Microfluor® 96-well plates (Dynex). 30 $\mu$L of a "stop" buffer is then added, which consists of 100 mM HEPES, pH 7.5, 300 mM NaCl, 20 mM EDTA, 1% SDS, and a biotinylated oligonucleotide (complementary to the substrate oligonucleotide) at 20 nM. After 1.5 h at room temperature, 50 $\mu$L of a suspension of streptavidin-coated polyvinyl toluene SPA beads (1.25 mg/mL in 50 mM HEPES, pH 7.5, 0.02% NaN$_3$) is added, followed by a further 0.5 h incubation at room temperature. Assay plates are then centrifuged briefly to pellet the SPA beads and the amount of reaction product is detected by scintillation counting using a Packard Topcount™.

Example 12: Inhibition of E1 Helicase Activity (IC$_{50}$ Curves)

To determine the potency of potential inhibitors, E1 helicase SPA reactions (Example 11) were run in the presence of serially diluted inhibitors. The concentrations of both M13 and ethidium bromide ranged from 0.04 to 20 $\mu$M.

Reaction controls with no inhibitor, and blanks with no inhibitor and no enzyme, were run simultaneously. Unwinding was detected as described above and results were fit to a logistic using the SAS software package. [SAS is a registered trademark of the SAS Institute, Inc. of Cary, N.C.].

Figure 7:
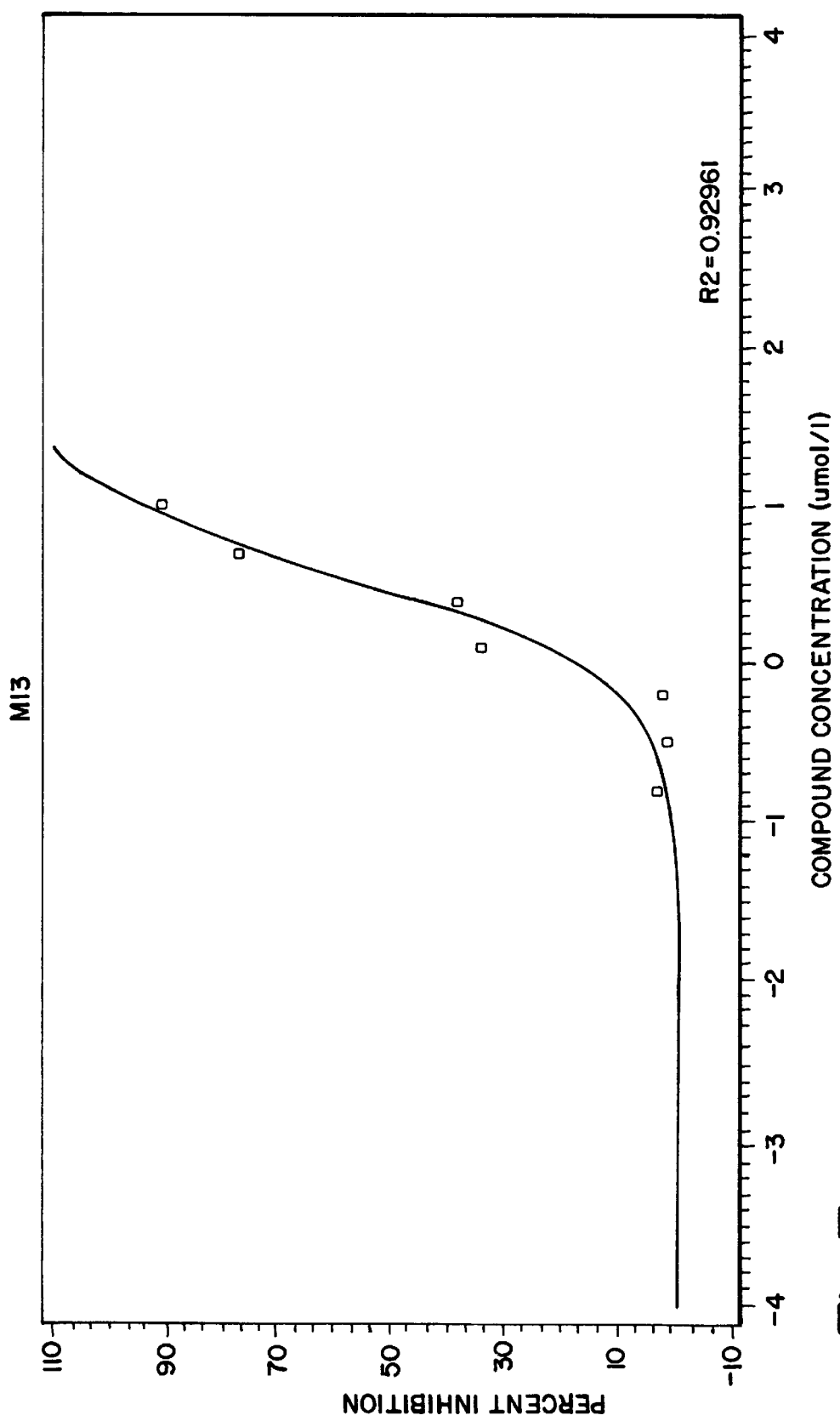
FIG. 7 shows the $IC_{50}$ curve for inhibition of the E1 helicase activity by the M13 plasmid as described in Example 12.
Figure 8:
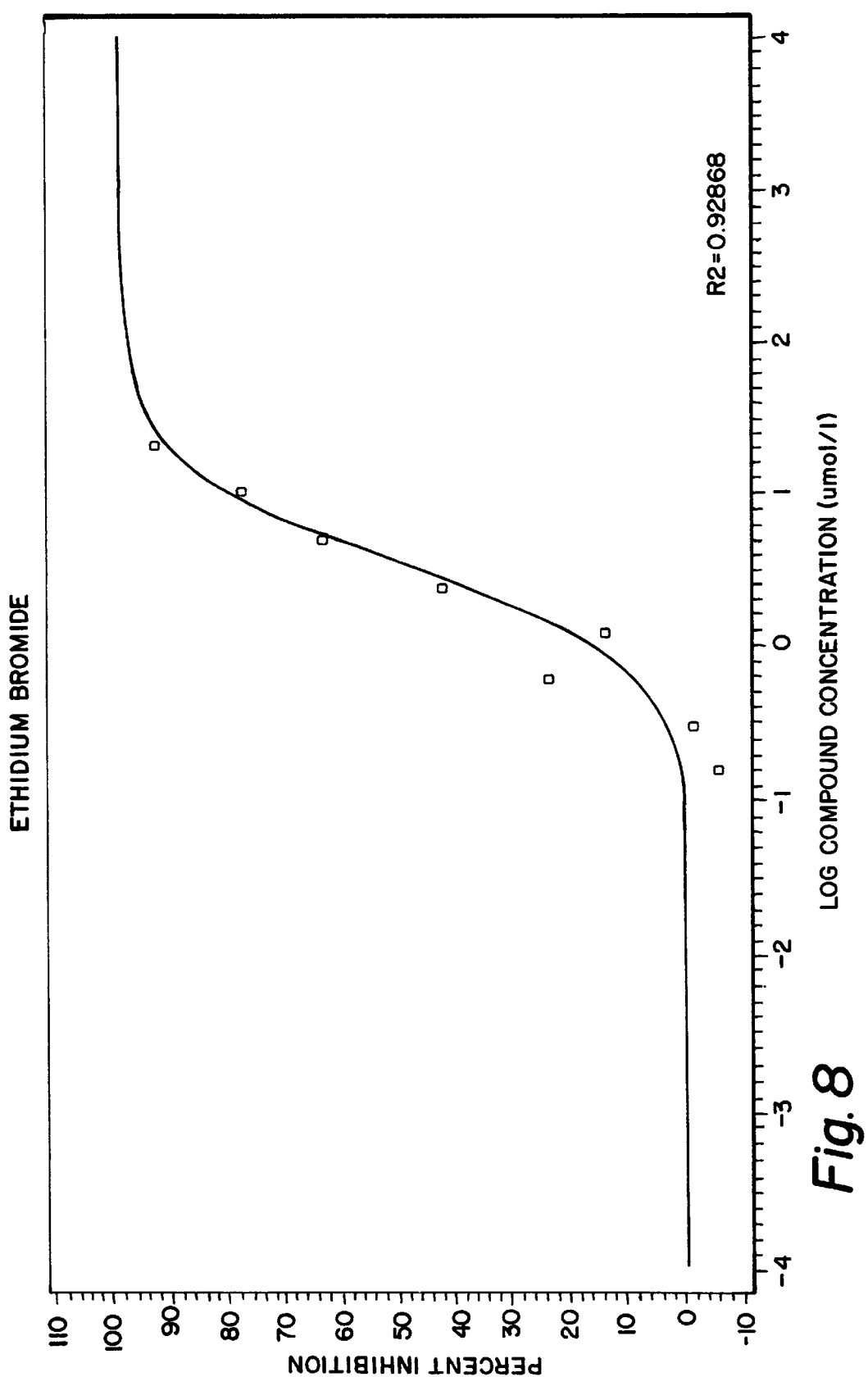
FIG. 8 shows the $IC_{50}$ curve of inhibition of the E1 helicase activity by ethidium bromide as described in Example 12.

For both FIGS. 7 and 8, data points are graphed as the percent inhibition at each inhibitor concentration. Concentration is expressed in $\mu$M on a log scale. Percent inhibition at each inhibitor concentration ([I]) is determined from the following formula:

$$100 - 100 \times \frac{\text{(activity at } [I] - \text{blank)}}{\text{(control activity} - \text{blank)}}$$

The solid line shows the best fit to the data determined by SAS. Some data points are out of range and are not shown in the figures.

From FIGS. 7 and 8, it can be approximated that the IC$_{50}$ are 3 and 4 $\mu$M respectively for M13 and ethidium bromide.

Example 13: HPV-6 E1 Expression

Construction of recombinant plasmid

Recombinant baculovirus construct (Bac-to-Bac system): E1 gene from HPV type 6a was PCR-amplified using recombinant plasmid pCR3.1-E1 (6a) as DNA template previously constructed in our lab from DNA isolated from a clinical sample. The forward primer was 5'-CGC GGA TCC AGG ATG CAT CAC CAT CAC CAT CACGCG GAC GAT TCA CGT ACA GAA AAT GAG 3' (SEQ ID NO.1) and the reverse one was GG CTG AAT TCA TAA AGT TCT AAC AAC T (SEQ ID NO.2). The resulting PCR fragment was then purified and restricted with EcoRI and BamHI and ligated with donor plasmid pFASTBAC1 linearized with the same enzymes.

HPV-6 E1 protein expression

HIS-E1-pFASTBAC was then transformed in *E. coli* DH10Bac® strain for transposition following the manufacturer's instructions (Gibco-BRL). White colonies were first selected and transposition confirmed by analytical PCR using primers flanking the insertion site in bacmid (baculovirus circular DNA).

Mini-preparation of recombinant bacmids was conducted and then transfected in SF9 cell. 72 h post-transfection, baculovirus-containing supernatants were collected and infected cells resuspended in 2× Leammli buffer for expression analysis by Western using K72 polyclonal antibody. Recombinant baculovirus confirmed to express ELHIS was reamplified and further used to infect SF21 cells for large scale production.

Example 14: HPV-11 and HPV-6a His-E1 Extraction Using Different Concentrations of Salt E1 extraction. SF21 insect cells infected with E1-pFASTBAC recombinant baculovirus were harvested from 5 L culture in SF-900 II SFM medium to give a cell pellet of 65 ml which has been frozen rapidly in dry ice. Frozen pellet was then thawed rapidly and cells resuspended in 65 ml of cell lysis buffer A (20 mM tris, pH 8.0, 1 mM DTT, 1 mM EDTA, 5 mM KCl, 1mM MgCl$_2$—antipain, leupeptin and pepstatin each at 1 μg/ml–1 mM Pefabloc™). Following 15 min incubation on ice, cells were broken with a Dounce homogenizer (≈5 min, pestle B) and then centrifuged at 2500 g, 20 min, 4°. Supernatant was recentrifuged at 148 000 g, 4° for 45 min and this second supernatant was kept as "cytosol". Glycerol was added to this supernatant to 10% final concentration and this sample was frozen rapidly on dry ice and stored at –80°. Pelleted nuclei were resuspended to 90 ml with extraction buffer A (20 mM Tris pH 8, 5 mm β-mercaptoethanol, 2 mM Pefabloc™, 2 μg/ml pepstatin, 2 μg/ml leupeptin, and 2 μg/ml antipain) and distributed in 18 ml aliquots in 5 tubes. 18 ml of extraction buffer B (20 mM Tris pH 8, 5 mM β-mercaptoethanol, and 0.02% Triton X-100) was added and NaCl concentration was adjusted with a 5M solution to the conditions listed below. Samples were incubated at 4° with rocking for 30 min and centrifuged at 148000 g, 4° for 45 min. Supernatants were finally recovered and glycerol was added to the supernatant to 10% final concentration and the extract was frozen rapidly on dry ice and stored at –80°.

Example 15: HPV-11 and HPV-6a His-E1 Purification.

Nuclear extracts were thawed rapidly and the NaCl concentration adjusted to 500 mM before the preparation was loaded on 1 ml Hi-Trap™ chelating column previously charged with NiSO$_4$ according to the Manufacturer's instructions (Pharmacia, Biotech). The column was then pre-equilibrated in equilibration buffer (20 mM Tris pH 8, 5 mM β-mercaptoethanol, 500 mM NaCl, 10 mM imidazole, and 10% glycerol) and the flow-through collected for analysis. The column was washed first with 5–6 volumes of equilibration buffer and then with 5–6 volumes of washing buffer (equilibration buffer but with 50 mM imidazole) before His-E1 was eluted (1 mL fractions 1 to 10) with elution buffer (equilibration buffer but with 180 mM imidazole). E1 proteins were then dialyzed in dialysis buffer (20 mM MES pH 7.0, 500 mM NaCl, 1 mM DTT, 0.05 mM EDTA, and 10% glycerol) before being frozen on dry ice and stored at –80°.

For load and flow-through samples, 4 μl of each fractions were run on 10% SDS-PAGE). For each comparison experiment, 1 gel was stained with Coomassie Blue (FIG. 9A) and another one transferred for the membrane to be hybridized with anti-E1 K72 polyclonal antibody and detected with "western blot chemiluminescent reagent" (DuPont NEN, Boston, Mass.) and the emitted light was captured on autoradiography film (FIG. 9B).

Figure 9A:
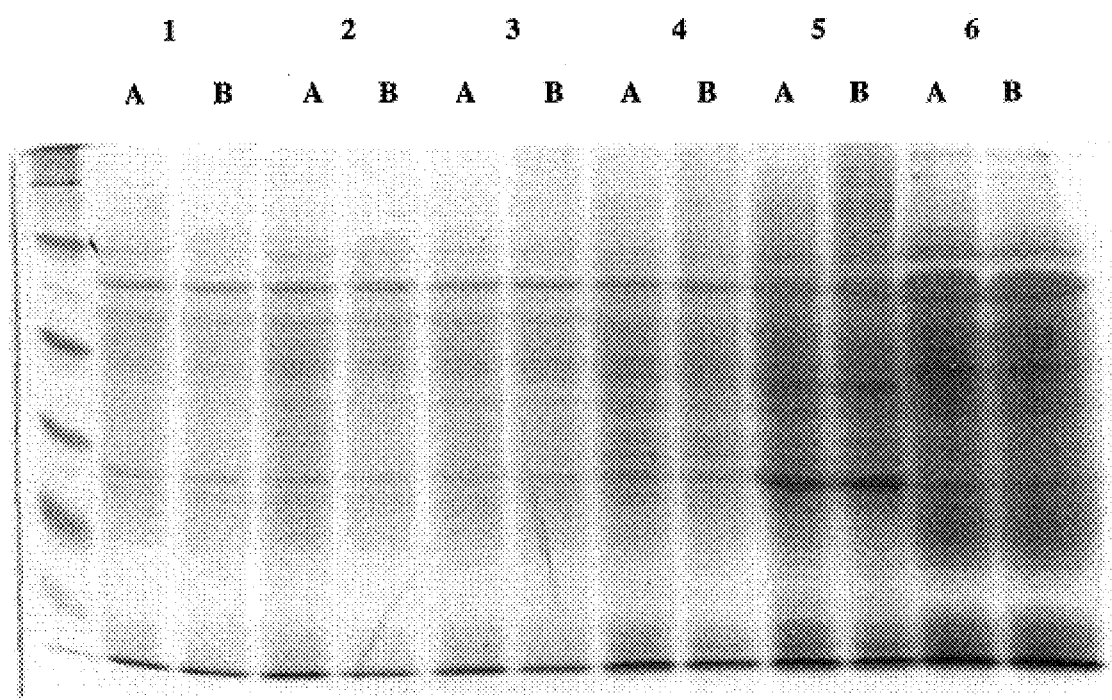
FIG. 9A shows a Coomassie blue-stained gel of the loaded material and the different fractions recovered from the affinity-chromatography purification (the legend of which is presented in Example 14)

Legends of FIGS. 9A (Coomassie) and 9B (Western blot):
A: load on Hi-Trap column (Crude Extract)
B: Flow through from Hi-Trap column
Lane 1: HPV-11 E1 extracted in absence of NaCl
Lane 2: HPV-11 E1 extracted with 50 mM NaCl
Lane 3: HPV-11 E1 extracted with 100 mM NaCl
Lane 4: HPV-11 E1 extracted with 250 mM NaCl
Lane 5: HPV-11 E1 extracted with 500 mM NaCl
Lane 6: HPV-11 E1 extracted from cytosol FIG. 9A shows a Coomassie blue-stained gel of crude E1 extract obtained from the protocol of Example 14. Lanes 4 and 5 reveal that there is a lot more material extracted at 250 and 500 mM salt but most of that material is not retained on the column, indicating that the majority of the material extracted at these salt concentrations is not E1.

Figure 9B:
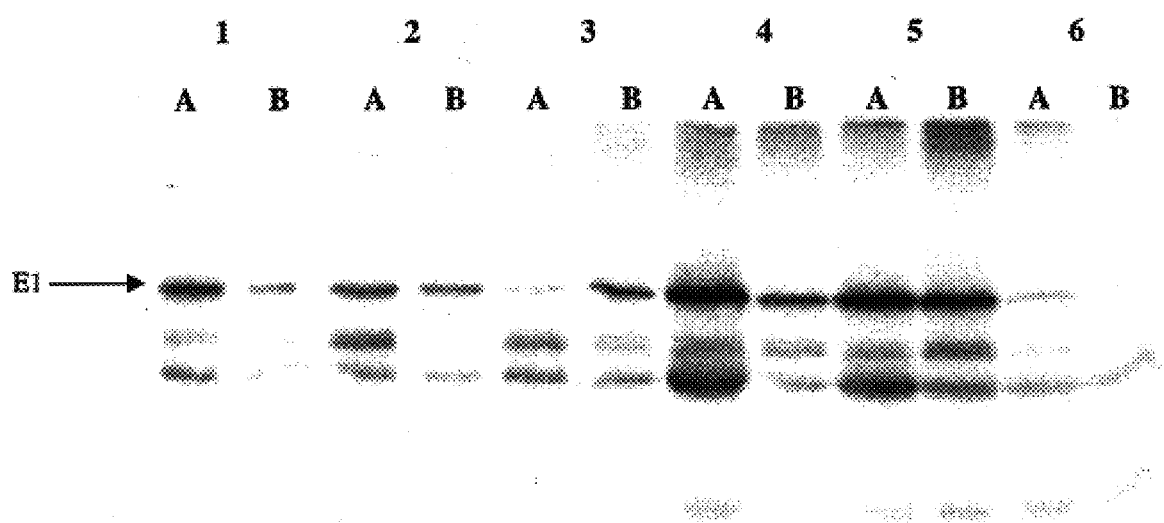
FIG. 9B shows a Western immunoblot of the gel of the different fractions recovered from the affinity-chromatography purification (the legend of which is presented in Example 15)

FIG. 9B allowed us to see that most of the E1 bound to he column. Once again the results of this experiment are in agreement with example 4.

Figure 10A:
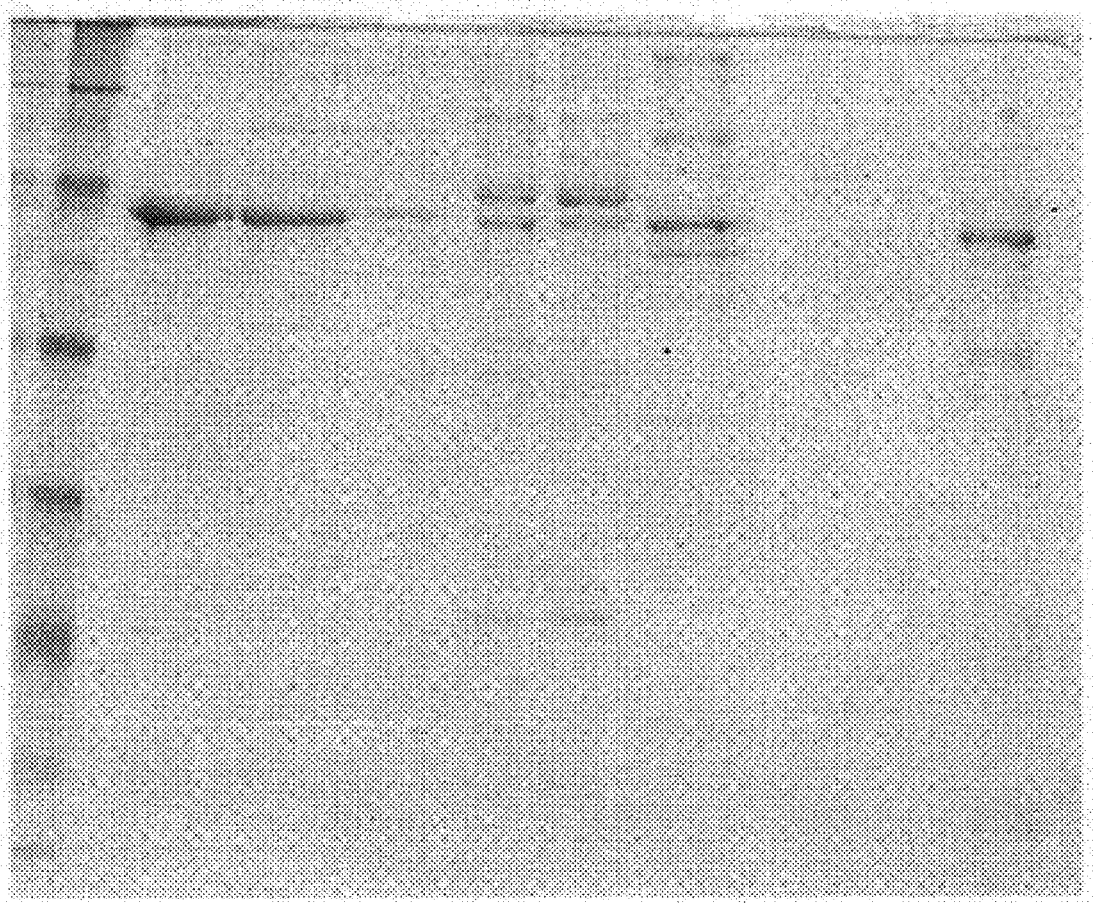
FIG. 10A shows a Coomassie blue-stained gel of different conditions for the nuclear extraction of the E1 protein (the legend of which is presented in Example 15) and also the no-salt extraction of HPV-6 E1 protein.
Figure 10B:
FIG. 10B shows a Western immunoblot of the gel of FIG. 9A. The blot was incubated with an anti-E1 polyclonal antibody and horseradish peroxidase (HRP)-conjugated second antibody. Bands were visualized using a chemiluminescent reagent.

Bradford protein assay was performed on elution fractions and SDS-PAGE and western blot of purified E1 were done with a content amount of total protein (1 μg for SDS-PAGE; 0.2 μg for western) (FIGS. 10A, 10B).

FIGS. 10A Legend:
SDS-PAGE purified E1
Lane 1: HPV-11 E1 extracted in absence of NaCl
Lane 2: HPV-11 E1 extracted with 50 mM NaCl
Lane 3: HPV-11 E1 extracted with 100 mM NaCl
Lane 4: HPV-11 E1 extracted with 250 mM NaCl
Lane 5: HPV-11 E1 extracted with 500 mM NaCl
Lane 6: HPV-11 E1 extracted from cytosol
Lane 7: HPV-6a E1 extracted in absence of NaCl
FIGS. 10B Legend:
Western Blot of purified E1
Lane 1: HPV-11 E1 extracted in absence of NaCl
Lane 2: HPV-11 E1 extracted with 50 mM NaCl
Lane 3: HPV-11 E1 extracted with 100 mN NaCl
Lane 4: HPV-11 E1 extracted with 250 mM NaCl
Lane 5: HPV-11 E1 extracted with 500 mM NaCl
Lane 6: HPV-11 E1 extracted from cytosol
Lane 7: HPV-6a E1 extracted in absence of NaCl FIGS. 10A and 10B reproduce and extend the results of example 3 where, as salt concentrations increase, the nuclear preparation is less pure and the preparation from the column is also less pure. In absence of salt and at 50 mM almost all of the E1 protein is already extracted. Concentrations of 100 mM and over do not improve the extraction of E1. Lane 6 also shows clearly that the extraction and purification of HPV-6 E1 is as effective in the absence of salt.

It was therefore established that the conditions for routine extraction would be performed at a salt concentration equal or lower than 300 mM for optimal results, preferably in hypotonic conditions equal or lower than 100 mM, more preferably equal or lower than 50 mM, and most preferably in the absence thereof.

The E1 proteins from HPV-11 and HPV-6a were sequenced and showed minor amino acid changes from the published literature. Our sequences are presented in FIG. 11 (as SEQ ID NO.26) for HPV-11, and in FIG. 12 (SEQ ID NO.27) for HPV-6a.

What is claimed is:

1. A method for isolating recombinant papillomavirus E1 protein having quantifiable unwinding activity comprising the steps of:
   producing an E1 recombinant protein in a eukaryotic expression system and isolating a nuclei preparation thereof; and
   extracting E1 recombinant protein from said nuclei preparation in a buffer comprising salt at a concentration equal to or below isotonic concentration.

2. The method of claim 1, further comprising the step of:
   purifying E1 recombinant protein from said nuclear extract by affinity chromatography.

3. The method of claim 1, wherein said E1 is purified from a nuclei preparation in the presence of 0–100 mM salt.

4. The method of claim 1, wherein said E1 is purified from a nuclei preparation in the presence of 0–50 mM salt.

5. The method of claim 1, wherein said E1 is purified from a nuclei preparation in the absence of salt.

6. The method according to claim 1, wherein said salt is NaCl.

7. The method of claim 1, wherein said recombinant E1 protein is the E1 helicase from cottontail rabbit papillomavirus (CRPV), bovine papillomavirus (BPV) or human papillomavirus (HPV).

8. The method of claim 7, wherein said recombinant E1 protein is from HPV low risk or high risk types.

9. The method of claim 7, wherein said recombinant E1 protein is from a low risk type HPV selected from the group consisting of: type 6, type 11 and type 13.

10. The method of claim 9, wherein said low risk HPV is type 11 or type 6.

11. The method of claim 8, wherein said recombinant HPV E1 protein is from a high risk type HPV selected from the group consisting of types 16, 18, 31, 33, 35, 45, 52, or 58.

12. The method of claim 11, wherein said high risk HPV is type 16.

13. The method of claim 1, wherein said eukaryotic expression system is selected from the group consisting of: baculovirus in insect cells; Vaccinia, Sindbis, Semliki forest viruses, or Adenovirus in mammalian cells; and plasmid in yeast expression systems.

14. The method of claim 13, wherein said eukaryotic expression system is insect cells infected with a baculovirus.

15. The method of claim 1, wherein said E1 protein comprises an affinity label.

16. The method of claim 15, wherein said affinity label is selected from the group consisting of: histidine tag, glutathione-S-transferase, and maltose-binding-protein.

17. The method of claim 16, wherein said affinity label is recognized by an affinity ligand selected from the group consisting of: antibody, metal, maltose and glutathione.

18. The method of claim 17, wherein said affinity label is positioned at the N-terminus of said E1 protein.

19. The method of claim 17, wherein said antibody is a monoclonal or a polyclonal antibody.

20. The method of claim 17, wherein said E1 protein is labeled with a histidine-tag and said metal affinity ligand is a nickel column.

21. A method for assaying the unwinding activity of a papillomavirus E1 protein obtained according to the method of claim 1, comprising the steps of:

incubating said E1 protein with a suitable substrate for said unwinding activity; and quantifying the unwinding activity of said E1 protein.

22. The assay according to claim 21, wherein said papillomavirus is HPV-11 or HPV-6.

23. The assay of claim 21, wherein said E1 protein is selected from the group consisting of: SEQ ID NO. 13; SEQ ID NO. 14; SEQ ID NO. 15; SEQ ID NO. 16; SEQ ID NO. 17; SEQ ID NO. 18; SEQ ID NO. 19; SEQ ID NO. 20; SEQ ID NO. 26; and SEQ ID NO. 27.

* * * * *

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 1:

```
CGCGGATCCA GGATGCATCA CCATCACCAT CACGCGGACG ATTCACGTAC AGAAAATGAG      60
```

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
GGCTGAATTC ATAAAGTTCT AACAACT                                         27
```

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
CCTGACACTG GGAAGTCGTG CTTTTGC                                         27
```

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CCTGACACTG GGGAGTCGTG CTTTTGC                                         27
```

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
CCTGACACTG GGGCGTCGTG CTTTTGC                                         27
```

(2) INFORMATION FOR SEQ ID NO: 6:

(i) SEQUENCE CHARACTERISTICS:
        (A) LENGTH: 27 base pairs

```
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 6:

CCTGACACTG GGCACTCGTG CTTTTGC                                              27

(2) INFORMATION FOR SEQ ID NO: 7:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 7:

CCTGACACTG GGATCTCGTG CTTTTGC                                              27

(2) INFORMATION FOR SEQ ID NO: 8:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 8:

CCTGACACTG GGCGGTCGTG CTTTTGC                                              27

(2) INFORMATION FOR SEQ ID NO: 9:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 9:

AGTGACCGAA AACGGTCGGG ACCGAAAACG GTGTAGACCG AAAACGGTGT A                   51

(2) INFORMATION FOR SEQ ID NO: 10:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 10:

CTACACCGTT TTCGGTCTAC ACCGTTTTCG GTCCCGACCG TTTTCGGTCA CT                  52

(2) INFORMATION FOR SEQ ID NO: 11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear
```

(ii) MOLECULE TYPE: cDNA (xi) SEQUENCE DESCRIPTION: SEQ ID NO: 11:

GTAAAACGAC CAGTGCCAAG C                                           21

(2) INFORMATION FOR SEQ ID NO: 12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

TTCCCAGTCA CGACGTTGT                                              19

(2) INFORMATION FOR SEQ ID NO: 13:

(i) SEQUENCE CHARACTERISTICS:
        (A) LENGTH: 649 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 13:

```
Met Ala Asp Asp Ser Gly Thr Glu Asn Glu Gly Ser Gly Cys Thr Gly
 1               5                  10                  15

Trp Phe Met Val Glu Ala Ile Val His Thr Thr Gly Thr Gln Ile
            20                  25                  30

Ser Glu Asp Glu Glu Glu Val Glu Asp Ser Gly Tyr Asp Met Val
            35                  40                  45

Asp Phe Ile Asp Asp Arg His Ile Thr Gln Asn Ser Val Glu Ala Gln
    50                  55                  60

Ala Leu Phe Asn Arg Gln Glu Ala Asp Ala His Tyr Ala Thr Val Gln
 65                 70                  75                  80

Asp Leu Lys Arg Lys Tyr Leu Gly Ser Pro Tyr Val Ser Pro Ile Ser
                85                  90                  95

Asn Val Ala Asn Ala Val Glu Ser Glu Ile Ser Pro Arg Leu Asp Ala
            100                 105                 110

Ile Lys Leu Thr Thr Gln Pro Lys Lys Val Lys Arg Arg Leu Phe Glu
            115                 120                 125

Thr Arg Glu Leu Thr Asp Ser Gly Tyr Gly Tyr Ser Glu Val Glu Ala
    130                 135                 140

Ala Thr Gln Val Glu Lys His Gly Asp Pro Glu Asn Gly Gly Asp Gly
145                 150                 155                 160

Gln Glu Arg Asp Thr Gly Arg Asp Ile Glu Gly Glu Val Glu His
                165                 170                 175

Arg Glu Ala Glu Ala Val Asp Asp Ser Thr Arg Glu His Ala Asp Thr
            180                 185                 190

Ser Gly Ile Leu Glu Leu Leu Lys Cys Lys Asp Ile Arg Ser Thr Leu
            195                 200                 205

His Gly Lys Phe Lys Asp Cys Phe Gly Leu Ser Phe Val Asp Leu Ile
            210                 215                 220

Arg Pro Phe Lys Ser Asp Arg Thr Thr Cys Ala Asp Trp Val Val Ala
225                 230                 235                 240
```

-continued

```
Gly Phe Gly Ile His His Ser Ile Ala Asp Ala Phe Gln Lys Leu Ile
            245                 250                 255

Glu Pro Leu Ser Leu Tyr Ala His Ile Gln Trp Leu Thr Asn Ala Trp
            260                 265                 270

Gly Met Val Leu Leu Val Leu Ile Arg Phe Lys Val Asn Lys Ser Arg
            275                 280                 285

Cys Thr Val Ala Arg Thr Leu Gly Thr Leu Leu Asn Ile Pro Glu Asn
290                 295                 300

His Met Leu Ile Glu Pro Pro Lys Ile Gln Ser Gly Val Arg Ala Leu
305                 310                 315                 320

Tyr Trp Phe Arg Thr Gly Ile Ser Asn Ala Ser Thr Val Ile Gly Glu
            325                 330                 335

Ala Pro Glu Trp Ile Thr Arg Gln Thr Val Ile Glu His Ser Leu Ala
            340                 345                 350

Asp Ser Gln Phe Lys Leu Thr Glu Met Val Gln Trp Ala Tyr Asp Asn
            355                 360                 365

Asp Ile Cys Glu Glu Ser Glu Ile Ala Phe Glu Tyr Ala Gln Arg Gly
            370                 375                 380

Asp Phe Asp Ser Asn Ala Arg Ala Phe Leu Asn Ser Asn Met Gln Ala
385                 390                 395                 400

Lys Tyr Val Lys Asp Cys Ala Ile Met Cys Arg His Tyr Lys His Ala
            405                 410                 415

Glu Met Lys Lys Met Ser Ile Lys Gln Trp Ile Lys Tyr Arg Gly Thr
            420                 425                 430

Lys Val Asp Ser Val Gly Asn Trp Lys Pro Ile Val Gln Phe Leu Arg
            435                 440                 445

His Gln Asn Ile Glu Phe Ile Pro Phe Leu Ser Lys Leu Lys Leu Trp
            450                 455                 460

Leu His Gly Thr Pro Lys Lys Asn Cys Ile Ala Ile Val Gly Pro Pro
465                 470                 475                 480

Asp Thr Gly Lys Ser Cys Phe Cys Met Ser Leu Ile Lys Phe Leu Gly
            485                 490                 495

Gly Thr Val Ile Ser Tyr Val Asn Ser Cys Ser His Phe Trp Leu Gln
            500                 505                 510

Pro Leu Thr Asp Ala Lys Val Ala Leu Leu Asp Asp Ala Thr Gln Pro
            515                 520                 525

Cys Trp Thr Tyr Met Asp Thr Tyr Met Arg Asn Leu Leu Asp Gly Asn
            530                 535                 540

Pro Met Ser Ile Asp Arg Lys His Arg Ala Leu Thr Leu Ile Lys Cys
545                 550                 555                 560

Pro Pro Leu Leu Val Thr Ser Asn Ile Asp Ile Ser Lys Glu Glu Lys
            565                 570                 575

Tyr Lys Tyr Leu His Ser Arg Val Thr Thr Phe Thr Phe Pro Asn Pro
            580                 585                 590

Phe Pro Phe Asp Arg Asn Gly Asn Ala Val Tyr Glu Leu Ser Asp Ala
            595                 600                 605

Asn Trp Lys Cys Phe Phe Glu Arg Leu Ser Ser Ser Leu Asp Ile Glu
            610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
            645
```

(2) INFORMATION FOR SEQ ID NO: 14:

(i) SEQUENCE CHARACTERISTICS:
        (A) LENGTH: 646 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14:

```
Met Ala Glu Asp Thr Gly Thr Asn Asn Glu Gly Thr Gly Cys Ser Gly
1               5                   10                  15

Trp Phe Leu Val Glu Ala Val Val Glu Arg Thr Thr Gly Gln Gln Ile
            20                  25                  30

Ser Asp Glu Asp Glu Thr Val Glu Asp Ser Gly Leu Asp Met Val
        35                  40                  45

Asp Phe Ile Asp Asp Arg Pro Ile Thr His Asn Ser Val Glu Ala Gln
    50                  55                  60

Ala Leu Leu Asn Glu Gln Glu Ala Asp Ala His Tyr Ala Ala Val Gln
65                  70                  75                  80

Asp Leu Lys Arg Lys Tyr Leu Gly Ser Pro Tyr Val Ser Pro Leu Gly
                85                  90                  95

His Val Glu Gln Ser Val Asp Cys Asp Ile Ser Pro Arg Leu Asp Ala
                100                 105                 110

Ile Lys Leu Ser Arg Asn Ser Lys Lys Val Lys Arg Arg Leu Phe Gln
            115                 120                 125

Ser Arg Glu Ile Thr Asp Ser Gly Tyr Gly Tyr Ser Glu Val Glu Ala
        130                 135                 140

Glu Thr Gln Val Glu Arg Asn Gly Glu Pro Glu Asn Asp Cys Gly Gly
145                 150                 155                 160

Gly Gly His Gly Arg Asp Lys Glu Gly Glu Gly Gln Val His Thr Glu
                165                 170                 175

Val His Thr Gly Ser Gln Ile Glu Glu His Thr Gly Thr Thr Arg Val
            180                 185                 190

Leu Glu Leu Leu Lys Cys Lys Asp Val Arg Ala Thr Leu Tyr Gly Lys
        195                 200                 205

Phe Lys Asp Cys Tyr Gly Leu Ser Phe Thr Asp Leu Ile Arg Pro Phe
    210                 215                 220

Lys Ser Asp Lys Thr Thr Cys Gly Asp Trp Val Val Ala Ala Phe Gly
225                 230                 235                 240

Ile His His Ser Val Ser Glu Ala Phe Glu Lys Leu Met Gln Pro Leu
                245                 250                 255

Thr Thr Tyr Met His Ile Gln Trp Leu Thr Asn Ala Trp Gly Met Val
            260                 265                 270

Leu Leu Val Leu Ile Arg Phe Lys Val Asn Lys Ser Arg Cys Thr Val
        275                 280                 285

Ala Arg Thr Leu Ala Thr Phe Leu Asn Ile Pro Glu Asp His Met Leu
    290                 295                 300

Ile Glu Pro Pro Lys Ile Gln Ser Ser Val Ala Ala Leu Tyr Trp Phe
305                 310                 315                 320

Arg Thr Gly Ile Ser Asn Ala Ser Ile Val Thr Gly Glu Thr Pro Glu
                325                 330                 335

Trp Ile Lys Arg Gln Thr Ile Val Glu His Gly Leu Ala Asp Asn Gln
            340                 345                 350

Phe Lys Leu Thr Glu Met Val Gln Trp Ala Tyr Asp Asn Asp Phe Cys
```

-continued

```
                355                 360                 365
Asp Glu Ser Glu Ile Ala Phe Glu Tyr Ala Gln Arg Gly Asp Phe Asp
            370                 375                 380
Ser Asn Ala Arg Ala Phe Leu Asn Ser Asn Cys Gln Ala Lys Tyr Val
385                 390                 395                 400
Lys Asp Cys Ala Thr Met Cys Lys His Tyr Lys Asn Ala Glu Met Lys
                405                 410                 415
Lys Met Ser Met Lys Gln Trp Ile Thr Tyr Arg Ser Lys Lys Ile Glu
            420                 425                 430
Glu Ala Gly Asn Trp Lys Pro Ile Val Gln Phe Leu Arg His Gln Asn
            435                 440                 445
Ile Glu Phe Ile Pro Phe Leu Ser Lys Leu Lys Leu Trp Leu His Gly
    450                 455                 460
Thr Pro Lys Lys Asn Cys Ile Ala Ile Val Gly Pro Pro Asp Thr Gly
465                 470                 475                 480
Lys Ser Cys Phe Cys Met Ser Leu Ile Lys Phe Leu Gly Gly Thr Val
                485                 490                 495
Ile Ser Tyr Val Asn Ser Ser His Phe Trp Leu Gln Pro Leu Cys
            500                 505                 510
Asn Ala Lys Val Ala Leu Leu Asp Asp Ala Thr Gln Ser Cys Trp Val
            515                 520                 525
Tyr Met Asp Thr Tyr Met Arg Asn Leu Leu Asp Gly Asn Pro Met Ser
    530                 535                 540
Ile Asp Arg Lys His Lys Ser Leu Ala Leu Ile Lys Cys Pro Pro Leu
545                 550                 555                 560
Leu Val Thr Ser Asn Val Asp Ile Thr Lys Asp Asp Lys Tyr Lys Tyr
                565                 570                 575
Leu Tyr Ser Arg Val Thr Thr Leu Thr Phe Pro Asn Pro Phe Pro Phe
            580                 585                 590
Asp Arg Asn Gly Asn Ala Val Tyr Glu Leu Ser Asp Ala Asn Trp Lys
            595                 600                 605
Cys Phe Phe Thr Arg Leu Ser Ala Ser Leu Asp Ile Gln Asp Ser Glu
    610                 615                 620
Asp Glu Asp Asp Gly Asp Asn Ser Gln Ala Phe Arg Cys Val Pro Gly
625                 630                 635                 640
Thr Val Val Arg Thr Val
                645

(2) INFORMATION FOR SEQ ID NO: 15:

(i) SEQUENCE CHARACTERISTICS:
        (A) LENGTH: 649 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 15:

Met Ala Asp Asp Ser Gly Thr Glu Asn Glu Gly Ser Gly Cys Thr Gly
1               5                   10                  15
Trp Phe Met Val Glu Ala Ile Val Gln His Pro Thr Gly Thr Gln Ile
                20                  25                  30
Ser Asp Asp Glu Asp Glu Glu Val Glu Asp Ser Gly Tyr Asp Met Val
            35                  40                  45
Asp Phe Ile Asp Asp Ser Asn Ile Thr His Asn Ser Leu Glu Ala Gln
```

-continued

```
            50                  55                  60
Ala Leu Phe Asn Arg Gln Glu Ala Asp Thr His Tyr Ala Thr Val Gln
 65                  70                  75                  80

Asp Leu Lys Arg Lys Tyr Leu Gly Ser Pro Tyr Val Ser Pro Ile Asn
                 85                  90                  95

Thr Ile Ala Glu Ala Val Glu Ser Glu Ile Ser Pro Arg Leu Asp Ala
            100                 105                 110

Ile Lys Leu Thr Arg Gln Pro Lys Lys Val Lys Arg Arg Leu Phe Gln
            115                 120                 125

Thr Arg Glu Leu Thr Asp Ser Gly Tyr Gly Tyr Ser Glu Val Glu Ala
130                 135                 140

Gly Thr Gly Thr Gln Val Glu Lys His Gly Val Pro Glu Asn Gly Gly
145                 150                 155                 160

Asp Gly Gln Glu Lys Asp Thr Gly Arg Asp Ile Glu Gly Glu His
                165                 170                 175

Thr Glu Ala Glu Ala Pro Thr Asn Ser Val Arg Glu His Ala Gly Thr
            180                 185                 190

Ala Gly Ile Leu Glu Leu Leu Lys Cys Lys Asp Leu Arg Ala Ala Leu
            195                 200                 205

Leu Gly Lys Phe Lys Glu Cys Phe Gly Leu Ser Phe Ile Asp Leu Ile
210                 215                 220

Arg Pro Phe Lys Ser Asp Lys Thr Thr Cys Leu Asp Trp Val Val Ala
225                 230                 235                 240

Gly Phe Gly Ile His His Ser Ile Ser Glu Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Leu Arg Phe Lys Val Asn Lys Ser Arg
            275                 280                 285

Ser Thr Val Ala Arg Thr Leu Ala Thr Leu Leu Asn Ile Pro Glu Asn
290                 295                 300

Gln Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Gly Leu Ala
            340                 345                 350

Asp Ser Gln Phe Lys Leu Thr Glu Met Val Gln Trp Ala Tyr Asp Asn
            355                 360                 365

Asp Ile Cys Glu Glu Ser Glu Ile Ala Phe Glu Tyr Ala Gln Arg Gly
370                 375                 380

Asp Phe Asp Ser Asn Ala Arg Ala Phe Leu Asn Ser Asn Met Gln Ala
385                 390                 395                 400

Lys Tyr Val Lys Asp Cys Ala Thr Met Cys Arg His Tyr Lys His Ala
                405                 410                 415

Glu Met Arg Lys Met Ser Ile Lys Gln Trp Ile Lys His Arg Gly Ser
            420                 425                 430

Lys Ile Glu Gly Thr Gly Asn Trp Lys Pro Ile Val Gln Phe Leu Arg
            435                 440                 445

His Gln Asn Ile Glu Phe Ile Pro Phe Leu Thr Lys Phe Lys Leu Trp
            450                 455                 460

Leu His Gly Thr Pro Lys Lys Asn Cys Ile Ala Ile Val Gly Pro Pro
465                 470                 475                 480
```

```
Asp Thr Gly Lys Ser Tyr Phe Cys Met Ser Leu Ile Ser Phe Leu Gly
            485                 490                 495
Gly Thr Val Ile Ser His Val Asn Ser Ser His Phe Trp Leu Gln
            500                 505                 510
Pro Leu Val Asp Ala Lys Val Ala Leu Leu Asp Asp Ala Thr Gln Pro
            515                 520                 525
Cys Trp Ile Tyr Met Asp Thr Tyr Met Arg Asn Leu Leu Asp Gly Asn
530                 535                 540
Pro Met Ser Ile Asp Arg Lys His Lys Ala Leu Thr Leu Ile Lys Cys
545                 550                 555                 560
Pro Pro Leu Leu Val Thr Ser Asn Ile Asp Ile Thr Lys Glu Asp Lys
            565                 570                 575
Tyr Lys Tyr Leu His Thr Arg Val Thr Thr Phe Thr Phe Pro Asn Pro
            580                 585                 590
Phe Pro Phe Asp Arg Asn Gly Asn Ala Val Tyr Glu Leu Ser Asn Thr
            595                 600                 605
Asn Trp Lys Cys Phe Phe Glu Arg Leu Ser Ser Ser Leu Asp Ile Gln
            610                 615                 620
Asp Ser Glu Asp Glu Glu Asp Gly Ser Asn Ser Gln Ala Phe Arg Cys
625                 630                 635                 640
Val Pro Gly Thr Val Val Arg Thr Leu
            645

(2) INFORMATION FOR SEQ ID NO: 16:

(i) SEQUENCE CHARACTERISTICS:
        (A) LENGTH: 657 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 16:

Met Ala Asp Pro Glu Gly Thr Asp Gly Glu Gly Thr Gly Cys Asn Gly
1               5                   10                  15
Trp Phe Tyr Val Gln Ala Ile Val Asp Lys Lys Thr Gly Asp Val Ile
            20                  25                  30
Ser Asp Asp Glu Asp Glu Asn Ala Thr Asp Thr Gly Ser Asp Met Val
            35                  40                  45
Asp Phe Ile Asp Thr Gln Gly Thr Phe Cys Glu Gln Ala Glu Leu Glu
        50                  55                  60
Thr Ala Gln Ala Leu Phe His Ala Gln Glu Val His Asn Asp Ala Gln
65                  70                  75                  80
Val Leu His Val Leu Lys Arg Lys Phe Ala Gly Gly Ser Thr Glu Asn
            85                  90                  95
Ser Pro Leu Gly Glu Arg Leu Glu Val Asp Thr Glu Leu Ser Pro Arg
            100                 105                 110
Leu Gln Glu Ile Ser Leu Asn Ser Gly Gln Lys Lys Ala Lys Arg Arg
            115                 120                 125
Leu Phe Thr Ile Ser Asp Ser Gly Tyr Gly Cys Ser Glu Val Glu Ala
            130                 135                 140
Thr Gln Ile Gln Val Thr Thr Asn Gly Glu His Gly Gly Asn Val Cys
145                 150                 155                 160
Ser Gly Gly Ser Thr Glu Ala Ile Asp Asn Gly Gly Thr Glu Gly Asn
            165                 170                 175
```

```
Asn Ser Ser Val Asp Gly Thr Ser Asp Asn Ser Asn Ile Glu Asn Val
            180                 185                 190

Asn Pro Gln Cys Thr Ile Ala Gln Leu Lys Asp Leu Leu Lys Val Asn
            195                 200                 205

Asn Lys Gln Gly Ala Met Leu Ala Val Phe Lys Asp Thr Tyr Gly Leu
            210                 215                 220

Ser Phe Thr Asp Leu Val Arg Asn Phe Lys Ser Asp Lys Thr Thr Cys
225                 230                 235                 240

Thr Asp Trp Val Thr Ala Ile Phe Gly Val Asn Pro Thr Ile Ala Glu
            245                 250                 255

Gly Phe Lys Thr Leu Ile Gln Pro Phe Ile Leu Tyr Ala His Ile Gln
            260                 265                 270

Cys Leu Asp Cys Lys Trp Gly Val Leu Ile Leu Ala Leu Leu Arg Tyr
            275                 280                 285

Lys Cys Gly Lys Ser Arg Leu Thr Val Ala Lys Gly Leu Ser Thr Leu
            290                 295                 300

Leu His Val Pro Glu Thr Cys Met Leu Ile Gln Pro Pro Lys Leu Arg
305                 310                 315                 320

Ser Ser Val Ala Ala Leu Tyr Trp Tyr Arg Thr Gly Ile Ser Asn Ile
            325                 330                 335

Ser Glu Val Met Gly Asp Thr Pro Glu Trp Ile Gln Arg Leu Thr Ile
            340                 345                 350

Ile Gln His Gly Ile Asp Asp Ser Asn Phe Asp Leu Ser Glu Met Val
            355                 360                 365

Gln Trp Ala Phe Asp Asn Glu Leu Thr Asp Glu Ser Asp Met Ala Phe
            370                 375                 380

Glu Tyr Ala Leu Leu Ala Asp Ser Asn Ser Asn Ala Ala Ala Phe Leu
385                 390                 395                 400

Lys Ser Asn Cys Gln Ala Lys Tyr Leu Lys Asp Cys Ala Thr Met Cys
            405                 410                 415

Lys His Tyr Arg Arg Ala Gln Lys Arg Gln Met Asn Met Ser Gln Trp
            420                 425                 430

Ile Arg Phe Arg Cys Ser Lys Ile Asp Glu Gly Gly Asp Trp Arg Pro
            435                 440                 445

Ile Val Gln Phe Leu Arg Tyr Gln Gln Ile Glu Phe Ile Thr Phe Leu
            450                 455                 460

Gly Ala Leu Lys Ser Phe Leu Lys Gly Thr Pro Lys Lys Asn Cys Leu
465                 470                 475                 480

Val Phe Cys Gly Pro Ala Asn Thr Gly Lys Ser Tyr Phe Gly Met Ser
            485                 490                 495

Phe Ile His Phe Ile Gln Gly Ala Val Ile Ser Phe Val Asn Ser Thr
            500                 505                 510

Ser His Phe Trp Leu Glu Pro Leu Thr Asp Thr Lys Val Ala Met Leu
            515                 520                 525

Asp Asp Ala Thr Thr Thr Cys Trp Thr Tyr Phe Asp Thr Tyr Met Arg
            530                 535                 540

Asn Ala Leu Asp Gly Asn Pro Ile Ser Ile Asp Arg Lys His Lys Pro
545                 550                 555                 560

Leu Ile Gln Leu Lys Cys Pro Pro Ile Leu Leu Thr Thr Asn Ile His
            565                 570                 575

Pro Ala Lys Asp Asn Arg Trp Pro Tyr Leu Glu Ser Arg Ile Thr Val
            580                 585                 590
```

```
Phe Glu Phe Pro Asn Ala Phe Pro Phe Asp Lys Asn Gly Asn Pro Val
            595                 600                 605
Tyr Glu Ile Asn Asp Lys Asn Trp Lys Cys Phe Phe Glu Arg Thr Trp
            610                 615                 620
Ser Arg Leu Asp Leu His Glu Glu Glu Asp Ala Asp Thr Glu Gly
625                 630                 635                 640
Asn Pro Phe Gly Thr Phe Lys Leu Arg Ala Gly Gln Asn His Arg Pro
                645                 650                 655
Leu
```

(2) INFORMATION FOR SEQ ID NO: 17:

(i) SEQUENCE CHARACTERISTICS:
        (A) LENGTH: 647 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 17:

```
Met Ala Asn Arg Glu Gly Thr Asp Gly Asp Gly Ser Gly Cys Asn Gly
1               5                   10                  15
Trp Phe Leu Val Gln Ala Ile Val Asp Lys Gln Thr Gly Asp Thr Val
                20                  25                  30
Ser Glu Asp Glu Asp Glu Asn Ala Thr Asp Thr Gly Ser Asp Leu Ala
                35                  40                  45
Asp Phe Ile Asp Asp Ser Thr Asp Ile Cys Val Gln Ala Glu Arg Glu
            50                  55                  60
Thr Ala Gln Val Leu Leu His Met Gln Glu Ala Gln Arg Asp Ala Gln
65                  70                  75                  80
Ala Val Arg Ala Leu Lys Arg Lys Tyr Thr Asp Ser Ser Gly Asp Thr
                85                  90                  95
Arg Pro Tyr Gly Lys Lys Val Gly Arg Asn Thr Arg Gly Thr Leu Gln
                100                 105                 110
Glu Ile Ser Leu Asn Val Ser Ser Thr Gln Ala Thr Gln Thr Val Tyr
                115                 120                 125
Ser Val Pro Asp Ser Gly Tyr Gly Asn Met Glu Val Glu Thr Ala Glu
                130                 135                 140
Val Glu Glu Val Thr Val Ala Thr Asn Thr Asn Gly Asp Ala Glu Gly
145                 150                 155                 160
Glu His Gly Gly Ser Val Arg Glu Glu Cys Ser Ser Val Asp Ser Ala
                165                 170                 175
Ile Asp Ser Glu Asn Gln Asp Pro Lys Ser Pro Thr Ala Gln Ile Lys
                180                 185                 190
Leu Leu Leu Gln Ser Asn Asn Lys Lys Ala Ala Met Leu Thr Gln Phe
                195                 200                 205
Lys Glu Thr Tyr Gly Leu Ser Phe Thr Asp Leu Val Arg Thr Phe Lys
                210                 215                 220
Ser Asp Lys Thr Thr Cys Thr Asp Trp Val Ala Ala Ile Phe Gly Val
225                 230                 235                 240
His Pro Thr Ile Ala Glu Gly Phe Lys Thr Leu Ile Asn Lys Tyr Ala
                245                 250                 255
Leu Tyr Thr His Ile Gln Ser Leu Asp Thr Lys Gln Gly Val Leu Ile
                260                 265                 270
Leu Met Leu Ile Arg Tyr Thr Cys Gly Lys Asn Arg Val Thr Val Gly
```

-continued

```
              275                 280                 285
Lys Gly Leu Ser Thr Leu Leu His Val Pro Glu Ser Cys Met Leu Leu
    290                 295                 300
Glu Pro Pro Lys Leu Arg Ser Pro Val Ala Ala Leu Tyr Trp Tyr Arg
305                 310                 315                 320
Thr Gly Ile Ser Asn Ile Ser Val Val Thr Gly Asp Thr Pro Glu Trp
                325                 330                 335
Ile Gln Arg Leu Thr Val Ile Gln His Gly Ile Asp Asp Ser Val Phe
            340                 345                 350
Asp Leu Ser Asp Met Val Gln Trp Ala Phe Asp Asn Glu Tyr Thr Asp
        355                 360                 365
Glu Ser Asp Ile Ala Phe Asn Tyr Ala Met Leu Ala Asp Cys Asn Ser
    370                 375                 380
Asn Ala Ala Phe Leu Lys Ser Asn Cys Gln Ala Lys Tyr Val Lys
385                 390                 395                 400
Asp Cys Ala Thr Met Cys Lys His Tyr Lys Arg Ala Gln Lys Arg Gln
                405                 410                 415
Met Ser Met Ser Gln Trp Ile Lys Phe Arg Cys Ser Lys Cys Asp Glu
            420                 425                 430
Gly Gly Asp Trp Arg Pro Ile Val Gln Phe Leu Arg Tyr Gln Gly Ile
        435                 440                 445
Glu Phe Ile Ser Phe Leu Cys Ala Leu Lys Glu Phe Leu Lys Gly Thr
    450                 455                 460
Pro Lys Lys Asn Cys Ile Val Ile Tyr Gly Pro Ala Asn Thr Gly Lys
465                 470                 475                 480
Ser His Phe Cys Met Ser Leu Met His Phe Leu Gln Gly Thr Val Ile
                485                 490                 495
Ser Tyr Val Asn Ser Thr Ser His Phe Trp Leu Glu Pro Leu Ala Asp
            500                 505                 510
Ala Lys Leu Ala Met Leu Asp Asp Ala Thr Gly Thr Cys Trp Ser Tyr
        515                 520                 525
Phe Asp Asn Tyr Met Arg Asn Ala Leu Asp Gly Tyr Ala Ile Ser Leu
    530                 535                 540
Asp Arg Lys Tyr Lys Ser Leu Leu Gln Met Lys Cys Pro Pro Leu Leu
545                 550                 555                 560
Ile Thr Ser Asn Thr Asn Pro Val Glu Asp Asp Arg Trp Pro Tyr Leu
                565                 570                 575
Arg Ser Arg Leu Thr Val Phe Lys Phe Pro Asn Ala Phe Pro Phe Asp
            580                 585                 590
Gln Asn Arg Asn Pro Val Tyr Thr Ile Asn Asp Lys Asn Trp Lys Cys
        595                 600                 605
Phe Phe Glu Lys Thr Trp Cys Arg Leu Asp Leu Gln Gln Asp Glu Asp
    610                 615                 620
Glu Gly Asp Asn Asp Glu Asn Thr Phe Thr Thr Phe Lys Cys Val Thr
625                 630                 635                 640
Gly Gln Asn Thr Arg Ile Leu
                645
```

(2) INFORMATION FOR SEQ ID NO: 18:

(i) SEQUENCE CHARACTERISTICS:
        (A) LENGTH: 644 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 18:

```
Met Ala Asp Pro Glu Gly Thr Asn Gly Ala Gly Met Gly Cys Thr Gly
  1               5                  10                  15

Trp Phe Glu Val Glu Ala Val Ile Glu Arg Arg Thr Gly Asp Asn Ile
                 20                  25                  30

Ser Glu Asp Glu Asp Glu Thr Ala Asp Asp Ser Gly Thr Asp Leu Leu
             35                  40                  45

Glu Phe Ile Asp Asp Ser Met Glu Asn Ser Ile Gln Ala Asp Thr Glu
         50                  55                  60

Ala Ala Arg Ala Leu Phe Asn Ile Gln Glu Gly Glu Asp Asp Leu Asn
 65              70                  75                  80

Ala Val Cys Ala Leu Lys Arg Lys Phe Ala Ala Cys Ser Gln Ser Ala
                 85                  90                  95

Ala Glu Asp Val Val Asp Arg Ala Ala Asn Pro Cys Arg Thr Ser Ile
                100                 105                 110

Asn Lys Asn Lys Glu Cys Thr Tyr Arg Lys Arg Lys Ile Asp Glu Leu
            115                 120                 125

Glu Asp Ser Gly Tyr Gly Asn Thr Glu Val Glu Thr Gln Gln Met Val
        130                 135                 140

Gln Gln Val Glu Ser Gln Asn Gly Asp Thr Asn Leu Asn Asp Leu Glu
145                 150                 155                 160

Ser Ser Gly Val Gly Asp Asp Ser Glu Val Ser Cys Glu Thr Asn Val
                165                 170                 175

Asp Ser Cys Glu Asn Val Thr Leu Gln Glu Ile Ser Asn Val Leu His
            180                 185                 190

Ser Ser Asn Thr Lys Ala Asn Ile Leu Tyr Lys Phe Lys Glu Ala Tyr
        195                 200                 205

Gly Ile Ser Phe Met Glu Leu Val Arg Pro Phe Lys Ser Asp Lys Thr
210                 215                 220

Ser Cys Thr Asp Trp Cys Ile Thr Gly Tyr Gly Ile Ser Pro Ser Val
225                 230                 235                 240

Ala Glu Ser Leu Lys Val Leu Ile Lys Gln His Ser Leu Tyr Thr His
                245                 250                 255

Leu Gln Cys Leu Thr Cys Asp Arg Gly Ile Ile Ile Leu Leu Leu Ile
            260                 265                 270

Arg Phe Arg Cys Ser Lys Asn Arg Leu Thr Val Ala Lys Leu Met Ser
        275                 280                 285

Asn Leu Leu Ser Ile Pro Glu Thr Cys Met Val Ile Glu Pro Pro Lys
        290                 295                 300

Leu Arg Ser Gln Thr Cys Ala Leu Tyr Trp Phe Arg Thr Ala Met Ser
305                 310                 315                 320

Asn Ile Ser Asp Val Gln Gly Thr Thr Pro Glu Trp Ile Asp Arg Leu
                325                 330                 335

Thr Val Leu Gln His Ser Phe Asn Asp Ile Phe Asp Leu Ser Glu
            340                 345                 350

Met Val Gln Trp Ala Tyr Asp Asn Glu Leu Thr Asp Asp Ser Asp Ile
        355                 360                 365

Ala Tyr Tyr Tyr Ala Gln Leu Ala Asp Ser Asn Ser Asn Ala Ala Ala
        370                 375                 380

Phe Leu Lys Ser Asn Ser Gln Ala Lys Ile Val Lys Asp Cys Gly Ile
385                 390                 395                 400
```

```
Met Cys Arg His Tyr Lys Lys Ala Glu Lys Arg Lys Met Ser Ile Gly
                405                 410                 415

Gln Trp Ile Gln Ser Arg Cys Glu Lys Thr Asn Asp Gly Gly Asn Trp
            420                 425                 430

Arg Pro Ile Val Gln Leu Leu Arg Tyr Gln Asn Ile Glu Phe Thr Ala
            435                 440                 445

Phe Leu Gly Ala Phe Lys Lys Phe Leu Lys Gly Ile Pro Lys Lys Ser
        450                 455                 460

Cys Met Leu Ile Cys Gly Pro Ala Asn Thr Gly Lys Ser Tyr Phe Gly
465                 470                 475                 480

Met Ser Leu Ile Gln Phe Leu Lys Gly Cys Val Ile Ser Cys Val Asn
                485                 490                 495

Ser Lys Ser His Phe Trp Leu Gln Pro Leu Ser Asp Ala Lys Ile Gly
            500                 505                 510

Met Ile Asp Asp Val Thr Pro Ile Ser Trp Thr Tyr Ile Asp Asp Tyr
        515                 520                 525

Met Arg Asn Ala Leu Asp Gly Asn Glu Ile Ser Ile Asp Val Lys His
        530                 535                 540

Arg Ala Leu Val Gln Leu Lys Cys Pro Pro Leu Leu Leu Thr Ser Asn
545                 550                 555                 560

Thr Asn Ala Gly Thr Asp Ser Arg Trp Pro Tyr Leu His Ser Arg Leu
                565                 570                 575

Thr Val Phe Glu Phe Lys Asn Pro Phe Pro Phe Asp Glu Asn Gly Asn
            580                 585                 590

Pro Val Tyr Ala Ile Asn Asp Glu Asn Trp Lys Ser Phe Phe Ser Arg
            595                 600                 605

Thr Trp Cys Lys Leu Asp Leu Ile Glu Glu Glu Asp Lys Glu Asn His
        610                 615                 620

Gly Gly Asn Ile Ser Thr Phe Lys Cys Ser Ala Gly Glu Asn Thr Arg
625                 630                 635                 640

Ser Leu Arg Ser (2) INFORMATION FOR SEQ ID NO: 19:

(i) SEQUENCE CHARACTERISTICS:
        (A) LENGTH: 629 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 19:

Met Ala Asp Pro Ala Gly Thr Asp Gly Glu Gly Thr Gly Cys Asn Gly
1               5                   10                  15

Trp Phe Tyr Val Glu Ala Val Ile Asp Arg Gln Thr Gly Asp Asn Ile
            20                  25                  30

Ser Glu Asp Glu Asn Glu Asp Ser Ser Asp Thr Gly Glu Asp Met Val
        35                  40                  45

Asp Phe Ile Asp Asn Cys Asn Val Tyr Asn Asn Gln Ala Glu Ala Glu
    50                  55                  60

Thr Ala Gln Ala Leu Phe His Ala Gln Glu Ala Glu His Ala Glu
65                  70                  75                  80

Ala Val Gln Val Leu Lys Arg Lys Tyr Val Gly Ser Pro Leu Ser Asp
                85                  90                  95
```

-continued

```
Ile Ser Ser Cys Val Asp Tyr Asn Ile Ser Pro Arg Leu Lys Ala Ile
            100                 105                 110
Cys Ile Glu Asn Asn Ser Lys Thr Ala Lys Arg Leu Phe Glu Leu
        115                 120                 125
Pro Asp Ser Gly Tyr Gly Asn Thr Glu Val Glu Thr Gln Gln Met Val
    130                 135                 140
Gln Val Glu Glu Gln Gln Thr Thr Leu Ser Cys Asn Gly Ser Asp Gly
145                 150                 155                 160
Thr His Ser Glu Arg Glu Asn Glu Thr Pro Thr Arg Asn Ile Leu Gln
                165                 170                 175
Val Leu Lys Thr Ser Asn Gly Lys Ala Ala Met Leu Gly Lys Phe Lys
            180                 185                 190
Glu Leu Tyr Gly Val Ser Phe Met Glu Leu Ile Arg Pro Phe Gln Ser
            195                 200                 205
Asn Lys Ser Thr Cys Thr Asp Trp Cys Val Ala Ala Phe Gly Val Thr
        210                 215                 220
Gly Thr Val Ala Glu Gly Phe Lys Thr Leu Leu Gln Pro Tyr Cys Leu
225                 230                 235                 240
Tyr Cys His Leu Gln Ser Leu Ala Cys Ser Trp Gly Met Val Met Leu
                245                 250                 255
Met Leu Val Arg Phe Lys Cys Ala Lys Asn Arg Ile Thr Ile Glu Lys
            260                 265                 270
Leu Leu Glu Lys Leu Leu Cys Ile Ser Thr Asn Cys Met Leu Ile Gln
        275                 280                 285
Pro Pro Lys Leu Arg Ser Thr Ala Ala Leu Tyr Trp Tyr Arg Thr
    290                 295                 300
Gly Met Ser Asn Ile Ser Asp Val Tyr Gly Glu Thr Pro Glu Trp Ile
305                 310                 315                 320
Glu Arg Gln Thr Val Leu Gln His Ser Phe Asn Asp Thr Thr Phe Asp
                325                 330                 335
Leu Ser Gln Met Val Gln Trp Ala Tyr Asp Asn Asp Val Met Asp Asp
            340                 345                 350
Ser Glu Ile Ala Tyr Lys Tyr Ala Gln Leu Ala Asp Ser Asp Ser Asn
        355                 360                 365
Ala Cys Ala Phe Leu Lys Ser Asn Ser Gln Ala Lys Ile Val Lys Asp
    370                 375                 380
Cys Gly Thr Met Cys Arg His Tyr Lys Arg Ala Glu Lys Arg Gln Met
385                 390                 395                 400
Ser Met Gly Gln Trp Ile Lys Ser Arg Cys Asp Lys Val Ser Asp Glu
                405                 410                 415
Gly Asp Trp Arg Asp Ile Val Lys Phe Leu Arg Tyr Gln Gln Ile Glu
            420                 425                 430
Phe Val Ser Phe Leu Ser Ala Leu Lys Leu Phe Leu Lys Gly Val Pro
        435                 440                 445
Lys Lys Asn Cys Ile Leu Ile His Gly Ala Pro Asn Thr Gly Lys Ser
    450                 455                 460
Tyr Phe Gly Met Ser Leu Ile Ser Phe Leu Gln Gly Cys Ile Ile Ser
465                 470                 475                 480
Tyr Ala Asn Ser Lys Ser His Phe Trp Leu Gln Pro Leu Ala Asp Ala
                485                 490                 495
Lys Ile Gly Met Leu Asp Asp Ala Thr Thr Pro Cys Trp His Tyr Ile
            500                 505                 510
Asp Asn Tyr Leu Arg Asn Ala Leu Asp Gly Asn Pro Val Ser Ile Asp
```

```
                515                 520                 525
Val Lys His Lys Ala Leu Met Gln Leu Lys Cys Pro Pro Leu Leu Ile
    530                 535                 540

Thr Ser Asn Ile Asn Ala Gly Lys Asp Asp Arg Trp Pro Tyr Leu His
545                 550                 555                 560

Ser Arg Leu Val Val Phe Thr Phe Pro Asn Pro Phe Pro Phe Asp Lys
                565                 570                 575

Asn Gly Asn Pro Val Tyr Glu Leu Ser Asp Lys Asn Trp Lys Ser Phe
            580                 585                 590

Phe Ser Arg Thr Trp Cys Arg Leu Asn Leu His Glu Glu Glu Asp Lys
        595                 600                 605

Glu Asn Asp Gly Asp Ser Phe Ser Thr Phe Lys Cys Val Ser Gly Gln
610                 615                 620

Asn Ile Arg Thr Leu
625
```

(2) INFORMATION FOR SEQ ID NO: 20:

(i) SEQUENCE CHARACTERISTICS:
        (A) LENGTH: 630 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 20:

```
Met Ala Asp Pro Ala Gly Thr Asp Glu Gly Glu Gly Thr Gly Cys Asn
1               5                   10                  15

Gly Trp Phe Phe Val Glu Ala Val Val Ser Arg Arg Thr Gly Ser Ser
                20                  25                  30

Val Glu Asp Glu Asn Glu Asp Asp Cys Asp Arg Gly Glu Asp Met Val
            35                  40                  45

Asp Phe Ile Asn Asp Thr Asp Ile Leu Asn Ile Gln Ala Glu Thr Glu
        50                  55                  60

Thr Ala Gln Ala Leu Phe His Ala Gln Glu Glu Gln Thr His Lys Glu
65                  70                  75                  80

Ala Val Gln Val Leu Lys Arg Lys Tyr Ala Ser Ser Pro Leu Ser Ser
                85                  90                  95

Val Ser Leu Cys Val Asn Asn Asn Ile Ser Pro Arg Leu Lys Ala Ile
                100                 105                 110

Cys Ile Glu Asn Lys Asn Thr Ala Ala Lys Arg Arg Leu Phe Glu Leu
            115                 120                 125

Pro Asp Ser Gly Tyr Gly Asn Ser Glu Val Glu Ile His Glu Ile Gln
130                 135                 140

Gln Val Glu Gly His Asp Thr Val Glu Gln Cys Ser Met Gly Ser Gly
145                 150                 155                 160

Asp Ser Ile Thr Ser Ser Ser Asp Glu Arg His Asp Glu Thr Pro Thr
            165                 170                 175

Arg Asp Ile Ile Gln Ile Leu Lys Cys Ser Asn Ala Asn Ala Ala Met
            180                 185                 190

Leu Ala Lys Phe Lys Glu Leu Phe Gly Ile Ser Phe Thr Glu Leu Ile
            195                 200                 205

Arg Pro Phe Lys Ser Asp Lys Ser Thr Cys Thr Asp Trp Cys Val Ala
            210                 215                 220

Ala Phe Gly Ile Ala Pro Ser Val Ala Asn Phe Lys His Ile Thr Tyr
```

```
                225                 230                 235                 240
        Val Tyr Ile Tyr Asn Val Tyr Arg Val His Gly Ala Met Val Ile Leu
                            245                 250                 255

Ala Leu Leu Arg Phe Lys Val Glu Lys Arg Glu Gln Gln Leu Lys Thr
                            260                 265                 270

Ile Asp Ala Lys Leu Leu Cys Ile Ser Ala Ala Ser Met Leu Ile Gln
                            275                 280                 285

Pro Pro Lys Leu Arg Ser Thr Pro Ala Ala Leu Tyr Trp Phe Lys Thr
                            290                 295                 300

Ala Met Ser Asn Ile Ser Glu Val Asp Gly Glu Thr Pro Glu Trp Ile
        305                 310                 315                 320

Gln Arg Gln Thr Val Leu Gln His Ser Phe Asn Asp Ala Ile Phe Asp
                            325                 330                 335

Leu Ser Glu Met Val Gln Trp Ala Tyr Asp Asn Asp Phe Ile Asp Asp
                            340                 345                 350

Ser Asp Ile Ala Tyr Lys Tyr Ala Gln Leu Ala Glu Thr Asn Ser Asn
                            355                 360                 365

Ala Cys Ala Phe Leu Lys Ser Asn Ser Gln Ala Lys Ile Val Lys Asp
                            370                 375                 380

Cys Ala Thr Met Cys Arg His Tyr Lys Arg Ala Glu Lys Arg Glu Met
        385                 390                 395                 400

Thr Met Ser Gln Trp Ile Lys Arg Arg Cys Ala Gln Val Asp Asp Asp
                            405                 410                 415

Gly Asp Trp Arg Asp Ile Val Arg Phe Leu Arg Tyr Gln Gln Val Asp
                            420                 425                 430

Phe Val Ala Phe Leu Ser Ala Leu Lys Asn Phe Leu His Gly Val Pro
                            435                 440                 445

Lys Lys Asn Cys Ile Leu Ile Tyr Gly Ala Pro Asn Thr Gly Lys Ser
        450                 455                 460

Leu Phe Gly Met Ser Leu Met His Phe Leu Gln Gly Ala Ile Ile Ser
        465                 470                 475                 480

Tyr Val Asn Ser Lys Ser His Phe Trp Leu Gln Pro Leu Tyr Asp Ala
                            485                 490                 495

Lys Ile Ala Met Leu Asp Asp Ala Thr Ser Pro Cys Gly Ile Tyr Arg
                            500                 505                 510

Pro Ile Phe Lys Lys Cys Thr Arg Trp Lys Ser Tyr Ile Ser Phe Arg
                            515                 520                 525

Cys Lys Ala Leu Ser Ile Val His Ile Met Pro Thr Phe Thr Tyr Tyr
        530                 535                 540

Ile Asn Ile Asn Ala Gly Lys Asp Asp Arg Trp Pro Tyr Leu His Ser
        545                 550                 555                 560

Arg Val Val Phe Thr Phe His Asn Glu Phe Pro Phe Asp Lys Asn
                            565                 570                 575

Gly Asn Pro Glu Tyr Gly Leu Asn Asp Lys Asn Trp Lys Ser Phe Phe
                            580                 585                 590

Ser Arg Thr Trp Cys Arg Leu Asn Leu His Glu Glu Val Lys Glu
                            595                 600                 605

Asn Asp Gly Asp Ala Phe Pro Ala Phe Lys Cys Val Ser Gly Gln Asn
                            610                 615                 620

Thr Arg Thr Leu Arg Asp
        625                 630

(2) INFORMATION FOR SEQ ID NO: 21:
```

(i) SEQUENCE CHARACTERISTICS:
    (A) LENGTH: 506 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 21:

```
Met Leu Gln Val Glu Gly Arg His Glu Thr Glu Thr Pro Cys Ser Gln
 1               5                  10                  15

Tyr Ser Gly Gly Ser Gly Gly Cys Ser Gln Tyr Ser Ser Gly Ser
                20                  25                  30

Gly Gly Glu Gly Val Ser Glu Arg His Thr Ile Cys Gln Thr Pro Leu
            35                  40                  45

Thr Asn Ile Leu Asn Val Leu Lys Thr Ser Asn Ala Lys Ala Ala Met
50                  55                  60

Leu Ala Lys Phe Lys Glu Leu Tyr Gly Val Ser Phe Ser Glu Leu Val
65                  70                  75                  80

Arg Pro Phe Lys Ser Asn Lys Ser Thr Cys Cys Asp Trp Cys Ile Ala
                85                  90                  95

Ala Phe Gly Leu Thr Pro Ser Ile Ala Asp Ser Ile Lys Thr Leu Leu
                100                 105                 110

Gln Gln Tyr Cys Leu Tyr Leu His Ile Gln Ser Leu Ala Cys Ser Trp
            115                 120                 125

Gly Met Val Val Leu Leu Val Arg Tyr Lys Cys Gly Lys Asn Arg
130                 135                 140

Glu Thr Ile Glu Lys Leu Leu Ser Lys Leu Leu Cys Val Ser Pro Met
145                 150                 155                 160

Cys Met Met Ile Glu Pro Pro Lys Leu Arg Ser Thr Ala Ala Ala Leu
                165                 170                 175

Tyr Trp Tyr Lys Thr Gly Ile Ser Asn Ile Ser Glu Val Tyr Gly Asp
                180                 185                 190

Thr Pro Glu Trp Ile Gln Arg Gln Thr Val Leu Gln His Ser Phe Asn
                195                 200                 205

Asp Cys Thr Phe Glu Leu Ser Gln Met Val Gln Trp Ala Tyr Asp Asn
210                 215                 220

Asp Ile Val Asp Asp Ser Glu Ile Ala Tyr Lys Tyr Ala Gln Leu Ala
225                 230                 235                 240

Asp Thr Asn Ser Asn Ala Ser Ala Phe Leu Lys Ser Asn Ser Gln Ala
                245                 250                 255

Lys Ile Val Lys Asp Cys Ala Thr Met Cys Arg His Tyr Lys Arg Ala
                260                 265                 270

Glu Lys Lys Gln Met Ser Met Ser Gln Trp Ile Lys Tyr Arg Cys Asp
            275                 280                 285

Arg Val Asp Asp Gly Gly Asp Trp Lys Gln Ile Val Met Phe Leu Arg
            290                 295                 300

Tyr Gln Gly Val Glu Phe Met Ser Phe Leu Thr Ala Leu Lys Arg Phe
305                 310                 315                 320

Leu Gln Gly Ile Pro Lys Lys Asn Cys Ile Leu Leu Tyr Gly Ala Ala
                325                 330                 335

Asn Thr Gly Lys Ser Leu Phe Gly Met Ser Leu Met Lys Phe Leu Gln
                340                 345                 350

Gly Ser Val Ile Cys Phe Val Asn Ser Lys Ser His Phe Trp Leu Gln
            355                 360                 365
```

```
Pro Leu Ala Asp Ala Lys Ile Gly Met Leu Asp Ala Thr Val Pro
    370                 375                 380

Cys Trp Asn Tyr Ile Asp Asp Asn Leu Arg Asn Ala Leu Asp Gly Asn
385                 390                 395                 400

Leu Val Ser Met Asp Val Lys His Arg Pro Leu Val Gln Leu Lys Cys
                405                 410                 415

Pro Pro Leu Leu Ile Thr Ser Asn Ile Asn Ala Gly Thr Asp Ser Arg
                420                 425                 430

Trp Pro Tyr Leu His Asn Arg Leu Val Val Phe Thr Phe Pro Asn Glu
            435                 440                 445

Phe Pro Phe Asp Glu Asn Gly Asn Pro Val Tyr Glu Leu Asn Asp Lys
450                 455                 460

Asn Trp Lys Ser Phe Phe Ser Arg Thr Trp Ser Arg Leu Ser Leu His
465                 470                 475                 480

Glu Asp Glu Asp Lys Glu Asn Asp Gly Asp Ser Leu Pro Thr Phe Lys
                485                 490                 495

Cys Val Ser Gly Gln Asn Thr Asn Thr Leu
            500                 505
```

(2) INFORMATION FOR SEQ ID NO: 22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

GCAAAAGCAC GACGCCCAG TGTCAGG                            27

(2) INFORMATION FOR SEQ ID NO: 23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

GCAAAAGCAC GAGTGCCCAG TGTCAGG                            27

(2) INFORMATION FOR SEQ ID NO: 24:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

GCAAAAGCAC GAGATCCCAG TGTCAGG                            27

(2) INFORMATION FOR SEQ ID NO: 25:

(i) SEQUENCE CHARACTERISTICS:
        (A) LENGTH: 27 base pairs
        (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO: 25:

GCAAAAGCAC GACCGCCCAG TGTCAGG                                               27

(2) INFORMATION FOR SEQ ID NO: 26:

(i) SEQUENCE CHARACTERISTICS:
        (A) LENGTH: 649 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 26:

Met Ala Asp Asp Ser Gly Thr Glu Asn Glu Gly Ser Gly Cys Thr Gly
1               5                   10                  15

Trp Phe Met Val Glu Ala Ile Val Glu His Thr Thr Gly Thr Gln Ile
            20                  25                  30

Ser Glu Asp Glu Glu Glu Val Glu Asp Ser Gly Tyr Asp Met Val
        35                  40                  45

Asp Phe Ile Asp Asp Arg His Ile Thr Gln Asn Ser Val Glu Ala Gln
50                  55                  60

Ala Leu Phe Asn Arg Gln Glu Ala Asp Ala His Tyr Ala Thr Val Gln
65                  70                  75                  80

Asp Leu Lys Arg Lys Tyr Leu Gly Ser Pro Tyr Val Ser Pro Ile Ser
                85                  90                  95

Asn Val Ala Asn Ala Val Glu Ser Glu Ile Ser Pro Arg Leu Asp Ala
            100                 105                 110

Ile Lys Leu Thr Thr Gln Pro Lys Val Lys Arg Arg Leu Phe Glu
        115                 120                 125

Thr Arg Glu Leu Thr Asp Ser Gly Tyr Gly Tyr Ser Glu Val Glu Ala
    130                 135                 140

Ala Thr Gln Val Glu Lys His Gly Asp Pro Glu Asn Gly Gly Asp Gly
145                 150                 155                 160

Glu Glu Arg Asp Thr Gly Arg Asp Ile Glu Gly Gly Val Glu His
                165                 170                 175

Arg Glu Ala Glu Ala Val Asp Asp Ser Thr Arg Glu His Ala Asp Thr
            180                 185                 190

Ser Gly Ile Leu Glu Leu Leu Lys Cys Lys Asp Ile Arg Ser Thr Leu
        195                 200                 205

His Gly Lys Phe Lys Asp Cys Phe Gly Leu Ser Phe Val Asp Leu Ile
    210                 215                 220

Arg Pro Phe Lys Ser Asp Arg Thr Thr Cys Ala Asp Trp Val Val Ala
225                 230                 235                 240

Gly Phe Gly Ile His His Ser Ile Ala Asp Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Ile Arg Phe Lys Val Asn Lys Ser Arg
        275                 280                 285

Cys Thr Val Ala Arg Thr Leu Gly Thr Leu Leu Asn Ile Pro Glu Asn
    290                 295                 300
```

His Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Ser Leu Ala
                340                 345                 350

Asp Ser Gln Phe Lys Leu Thr Glu Met Val Gln Trp Ala Tyr Asp Asn
                355                 360                 365

Asp Ile Cys Glu Glu Ser Glu Ile Ala Phe Glu Tyr Ala Gln Arg Gly
                370                 375                 380

Asp Phe Asp Ser Asn Ala Arg Ala Phe Leu Asn Ser Asn Met Gln Ala
385                 390                 395                 400

Lys Tyr Val Lys Asp Cys Ala Ile Met Cys Arg His Tyr Lys His Ala
                405                 410                 415

Glu Met Lys Lys Met Ser Ile Lys Gln Trp Ile Lys Tyr Arg Gly Thr
                420                 425                 430

Lys Val Asp Ser Val Gly Asn Trp Lys Pro Ile Val Gln Phe Leu Arg
                435                 440                 445

His Gln Asn Ile Glu Phe Ile Pro Phe Leu Ser Lys Leu Lys Leu Trp
450                 455                 460

Leu His Gly Thr Pro Lys Lys Asn Cys Ile Ala Ile Val Gly Pro Pro
465                 470                 475                 480

Asp Thr Gly Lys Ser Cys Phe Cys Met Ser Leu Ile Lys Phe Leu Gly
                485                 490                 495

Gly Thr Val Ile Ser Tyr Val Asn Ser Cys Ser His Phe Trp Leu Gln
                500                 505                 510

Pro Leu Thr Asp Ala Lys Val Ala Leu Leu Asp Asp Ala Thr Gln Pro
                515                 520                 525

Cys Trp Thr Tyr Met Asp Thr Tyr Met Arg Asn Leu Leu Asp Gly Asn
530                 535                 540

Pro Met Ser Ile Asp Arg Lys His Arg Ala Leu Thr Leu Ile Lys Cys
545                 550                 555                 560

Pro Pro Leu Leu Val Thr Ser Asn Ile Asp Ile Ser Lys Glu Glu Lys
                565                 570                 575

Tyr Lys Tyr Leu His Ser Arg Val Thr Thr Phe Thr Phe Pro Asn Pro
                580                 585                 590

Phe Pro Phe Asp Arg Asn Gly Asn Ala Val Tyr Glu Leu Ser Asp Ala
                595                 600                 605

Asn Trp Lys Cys Phe Phe Glu Arg Leu Ser Ser Ser Leu Asp Ile Glu
                610                 615                 620

Asp Ser Glu Asp Glu Glu Asp Gly Ser Asn Ser Gln Ala Phe Arg Cys
625                 630                 635                 640

Val Pro Gly Ser Val Val Arg Thr Leu
                645

(2) INFORMATION FOR SEQ ID NO: 27:

(i) SEQUENCE CHARACTERISTICS:
        (A) LENGTH: 649 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 27:

-continued

```
Met Ala Asp Asp Ser Gly Thr Glu Asn Glu Gly Ser Gly Cys Thr Gly
 1               5                  10                 15

Trp Phe Met Val Glu Ala Ile Val Gln His Pro Thr Gly Thr Gln Ile
            20                  25                  30

Ser Asp Asp Glu Asp Glu Glu Val Glu Asp Ser Gly Tyr Asp Met Val
        35                  40                  45

Asp Phe Ile Asp Asp Ser Asn Ile Thr His Asn Ser Leu Glu Ala Gln
    50                  55                  60

Ala Leu Phe Asn Arg Gln Glu Ala Asp Thr His Tyr Ala Thr Val Gln
65                  70                  75                  80

Asp Leu Lys Arg Lys Tyr Leu Gly Ser Pro Tyr Val Ser Pro Ile Asn
                85                  90                  95

Thr Ile Ala Glu Ala Val Glu Ser Glu Ile Ser Pro Arg Leu Asp Ala
            100                 105                 110

Ile Lys Leu Thr Arg Gln Pro Lys Lys Val Lys Arg Arg Leu Phe Gln
        115                 120                 125

Thr Arg Glu Leu Thr Asp Ser Gly Tyr Gly Tyr Ser Glu Val Glu Ala
    130                 135                 140

Gly Thr Gly Thr Gln Val Glu Lys His Gly Val Pro Glu Asn Gly Gly
145                 150                 155                 160

Asp Gly Gln Glu Lys Asp Thr Gly Arg Asp Ile Glu Gly Glu His
                165                 170                 175

Thr Glu Ala Glu Ala Pro Thr Asn Ser Val Arg Glu His Ala Gly Thr
            180                 185                 190

Ala Gly Ile Leu Glu Leu Leu Lys Cys Lys Asp Leu Arg Ala Ala Leu
        195                 200                 205

Leu Gly Lys Phe Lys Glu Cys Phe Gly Leu Ser Phe Ile Asp Leu Ile
    210                 215                 220

Arg Pro Phe Lys Ser Asp Lys Thr Thr Cys Leu Asp Trp Val Val Ala
225                 230                 235                 240

Arg Phe Gly Ile His His Ser Ile Ser Glu Ala Phe Gln Lys Leu Ile
                245                 250                 255

Glu Pro Leu Ser Leu Tyr Ala His Ile Gln Trp Leu Thr Asn Ala Trp
            260                 265                 270

Gly Met Val Leu Leu Val Leu Leu Arg Phe Lys Val Asn Lys Ser Arg
        275                 280                 285

Ser Thr Val Ala Arg Thr Leu Ala Thr Leu Leu Asn Ile Pro Glu Asn
    290                 295                 300

Gln Met Leu Ile Glu Pro Pro Lys Ile Gln Ser Gly Val Ala Ala Leu
305                 310                 315                 320

Tyr Trp Phe Arg Thr Gly Ile Ser Asn Ala Ser Thr Val Ile Gly Glu
                325                 330                 335

Ala Pro Glu Trp Ile Thr Arg Gln Thr Val Ile Glu His Gly Leu Ala
            340                 345                 350

Asp Ser Gln Phe Lys Leu Thr Glu Met Val Gln Trp Ala Tyr Asp Asn
        355                 360                 365

Asp Ile Cys Glu Glu Ser Glu Ile Ala Phe Glu Tyr Ala Gln Arg Gly
    370                 375                 380

Asp Phe Asp Ser Asn Ala Arg Ala Phe Leu Asn Ser Asn Met Gln Ala
385                 390                 395                 400

Lys Tyr Val Lys Asp Cys Ala Thr Met Cys Arg His Tyr Lys His Ala
                405                 410                 415

Glu Met Arg Lys Met Ser Ile Lys Gln Trp Ile Lys His Arg Gly Ser
```

-continued

```
                        420                     425                     430
Lys Ile Glu Gly Thr Gly Asn Trp Lys Pro Ile Val Gln Phe Leu Arg
            435                     440                     445

His Gln Asn Ile Glu Phe Ile Pro Phe Leu Thr Lys Phe Lys Leu Trp
        450                     455                     460

Leu His Gly Thr Pro Lys Lys Asn Cys Ile Ala Ile Val Gly Pro Pro
465                     470                     475                     480

Asp Thr Gly Lys Ser Tyr Phe Cys Met Ser Leu Ile Ser Phe Leu Gly
                485                     490                     495

Gly Thr Val Ile Ser His Val Asn Ser Ser Ser His Phe Trp Leu Gln
                500                     505                     510

Pro Leu Val Asp Ala Lys Val Ala Leu Leu Asp Asp Ala Thr Gln Pro
            515                     520                     525

Cys Trp Ile Tyr Met Asp Thr Tyr Met Arg Asn Leu Leu Asp Gly Asn
        530                     535                     540

Pro Met Ser Ile Asp Arg Lys His Lys Ala Leu Thr Leu Ile Lys Cys
545                     550                     555                     560

Pro Pro Leu Leu Val Thr Ser Asn Ile Asp Ile Thr Lys Glu Asp Lys
                565                     570                     575

Tyr Lys Tyr Leu His Thr Arg Val Thr Thr Phe Thr Phe Pro Asn Pro
            580                     585                     590

Phe Pro Phe Asp Arg Asn Gly Asn Ala Val Tyr Glu Leu Ser Asn Thr
        595                     600                     605

Asn Trp Lys Cys Phe Phe Glu Arg Leu Ser Ser Ser Leu Asp Ile Gln
    610                     615                     620

Asp Ser Glu Asp Glu Glu Asp Gly Ser Asn Ser Gln Ala Phe Arg Cys
625                     630                     635                     640

Val Pro Gly Thr Val Val Arg Thr Leu
                645
```